US012694497B2

(12) United States Patent
    Kakimoto et al.

(10) Patent No.: US 12,694,497 B2
(45) Date of Patent: Jul. 28, 2026

(54) EDIBLE OIL DETERIORATION DEGREE DETERMINATION DEVICE, EDIBLE OIL DETERIORATION DEGREE DETERMINATION SYSTEM, EDIBLE OIL DETERIORATION DEGREE DETERMINATION METHOD, EDIBLE OIL DETERIORATION DEGREE LEARNING DEVICE, AND LEARNED MODEL FOR USE IN EDIBLE OIL DETERIORATION DEGREE DETERMINATION

(71) Applicant: J-OIL MILLS, Inc., Tokyo (JP)

(72) Inventors: Kenichi Kakimoto, Tokyo (JP); Ryohei Watanabe, Tokyo (JP); Ayato Takasaki, Tokyo (JP); Masami Inoue, Tokyo (JP)

(73) Assignee: J-OIL MILLS, INC., Tokyo (JP)

( * ) Notice: Subject to any disclaimer, the term of this patent is extended or adjusted under 35 U.S.C. 154(b) by 351 days.

(21) Appl. No.: 18/691,537

(22) PCT Filed: Sep. 21, 2022

(86) PCT No.: PCT/JP2022/035127
    § 371 (c)(1),
    (2) Date: Mar. 13, 2024

(87) PCT Pub. No.: WO2023/054100
    PCT Pub. Date: Apr. 6, 2023

(65) Prior Publication Data
    US 2024/0386538 A1    Nov. 21, 2024

(30) Foreign Application Priority Data
    Sep. 29, 2021    (JP) ................................. 2021-160137

(51) Int. Cl.
    *G06T 7/00*        (2017.01)
    *G01N 33/03*       (2006.01)
    (Continued)

(52) U.S. Cl.
    CPC ........... *G06T 7/0002* (2013.01); *G01N 33/03* (2013.01); *G06V 10/26* (2022.01); *G06V 10/443* (2022.01); *G06V 10/56* (2022.01); *G06V 20/68* (2022.01)

(58) Field of Classification Search
    CPC .... G06T 7/0002; G06V 10/443; G06V 20/68; G06V 10/26; G06V 10/56; G01N 33/03
    See application file for complete search history.

(56) References Cited

U.S. PATENT DOCUMENTS

| | | | |
|---|---|---|---|
| 6,274,850 B1 | 8/2001 | Mercer | |
| 2019/0041375 A1* | 2/2019 | Yamasaki | ............... G01N 33/03 |
| 2022/0335548 A1* | 10/2022 | Suzuki | ............. G06Q 10/06314 |

FOREIGN PATENT DOCUMENTS

| | | | |
|---|---|---|---|
| JP | H08182624 A | | 7/1996 |
| JP | 3107499 B2 | * | 11/2000 |

(Continued)

*Primary Examiner* — Ming Shui
(74) *Attorney, Agent, or Firm* — RANKIN, HILL & CLARK LLP; Erik J. Overberger

(57)            ABSTRACT

Provided is an edible oil deterioration level determination device etc., which enable the types of surface air bubbles of frying oil to be accurately distinguished and thus the deterioration level of the frying oil to be accurately determined. An edible oil deterioration level determination device 5, comprising: an oil surface image acquisition section 50 configured to acquire an oil surface image; a filter processing section 53 configured to apply, to the oil surface, filter processing for identifying an area of fine air bubbles β characterizing deterioration of the frying oil Y; a feature parameter calculation section 54 configured to calculate a feature parameter characterizing the deterioration of the (Continued)

frying oil Y; a deterioration indicator estimation section 55 configured to estimate a deterioration indicator DI of the frying oil Y; and a deterioration level determination section 56 configured to determine the deterioration level of the frying oil Y.

11 Claims, 31 Drawing Sheets

(51) Int. Cl.
    *G06V 10/26*         (2022.01)
    *G06V 10/44*         (2022.01)
    *G06V 10/56*         (2022.01)
    *G06V 20/68*         (2022.01)

(56)              References Cited

FOREIGN PATENT DOCUMENTS

| | | | | |
|---|---|---|---|---|
| JP | 2003-250708 | A | | 9/2003 |
| JP | 2006177778 | A | * | 7/2006 |
| JP | 2017049030 | A | * | 3/2017 |
| JP | 2017-198717 | A | | 11/2017 |
| JP | 2020-38207 | A | | 3/2020 |
| WO | WO2021/053992 | A1 | | 3/2021 |
| WO | WO2021/059742 | A1 | | 4/2021 |

\* cited by examiner

CORRELATION BETWEEN AREA RATIO OF
ALL AIR BUBBLES AND COLOR

CORRELATION BETWEEN AREA RATIO OF
LARGE AIR BUBBLES AND COLOR

CORRELATION BETWEEN AREA RATIO OF
FINE AIR BUBBLES AND COLOR

CORRELATION BETWEEN AREA RATIO OF
ALL AIR BUBBLES AND ACID VALUE

AREA RATIO OF ALL AIR BUBBLES(%)

CORRELATION BETWEEN AREA RATIO OF
LARGE AIR BUBBLES AND ACID VALUE

AREA RATIO OF LARGE AIR BUBBLES(%)

CORRELATION BETWEEN AREA RATIO OF
FINE AIR BUBBLES AND ACID VALUE

AREA RATIO OF FINE AIR BUBBLES(%)

CORRELATION BETWEEN AREA RATIO OF ALL AIR
BUBBLES AND INCREASE RATE OF VISCOSITY

CORRELATION BETWEEN AREA RATIO OF LARGE AIR
BUBBLES AND INCREASE RATE OF VISCOSITY

CORRELATION BETWEEN AREA RATIO OF FINE AIR
BUBBLES AND INCREASE RATE OF VISCOSITY

CORRELATION BETWEEN NUMBER OF
ALL AIR BUBBLES AND COLOR

CORRELATION BETWEEN NUMBER OF
LARGE AIR BUBBLES AND COLOR

CORRELATION BETWEEN NUMBER OF
FINE AIR BUBBLES AND COLOR

CORRELATION BETWEEN NUMBER OF
ALL AIR BUBBLES AND ACID VALUE

CORRELATION BETWEEN NUMBER OF
LARGE AIR BUBBLES AND ACID VALUE

CORRELATION BETWEEN NUMBER OF
FINE AIR BUBBLES

CORRELATION BETWEEN NUMBER OF ALL AIR
BUBBLES AND INCREASE RATE OF VISCOSITY

CORRELATION BETWEEN NUMBER OF LARGE AIR
BUBBLES AND INCREASE RATE OF VISCOSITY

CORRELATION BETWEEN NUMBER OF FINE AIR
BUBBLES AND INCREASE RATE OF VISCOSITY

CORRELATION BETWEEN
AREA RATIO AND COLOR

CORRELATION BETWEEN
AREA RATIO AND ACID VALUE

CORRELATION BETWEEN AREA RATIO
AND INCREASE RATE OF VISCOSITY

CORRELATION BETWEEN NUMBER OF
AIR BUBBLES AND COLOR

CORRELATION BETWEEN NUMBER OF
AIR BUBBLES AND ACID VALUE

CORRELATION BETWEEN NUMBER OF AIR BUBBLES
AND INCREASE RATE OF VISCOSITY

CORRELATION BETWEEN STREAM
AND COLOR

COLOR(10R+Y)

STREAM OF FINE AIR BUBBLES

CORRELATION BETWEEN STREAM
AND ACID VALUE

ACID VALUE(mg/g)

STREAM OF FINE AIR BUBBLES

CORRELATION BETWEEN STREAM
AND INCREASE RATE OF VISCOSITY

INCREASE RATE OF
VISCOSITY(%)

STREAM OF FINE AIR BUBBLES

CORRELATION BETWEEN DISAPPEARANCE
SPEED AND COLOR

CORRELATION BETWEEN DISAPPEARANCE
SPEED AND ACID VALUE

CORRELATION BETWEEN DISAPPEARANCE
SPEED AND INCREASE RATE OF VISCOSITY

CORRELATION BETWEEN CONTOUR OF
DEEP-FRIED FOOD AND COLOR

CORRELATION BETWEEN CONTOUR OF
DEEP-FRIED FOOD AND ACID VALUE

CORRELATION BETWEEN CONTOUR OF DEEP-FRIED
FOOD AND INCREASE RATE OF VISCOSITY

CORRELATION BETWEEN CUMULATIVE VALUE
OF AREA OF AIR BUBBLES AND COLOR

CUMULATIVE VALUE OF AREA OF AIR BUBBLES

CORRELATION BETWEEN CUMULATIVE VALUE
OF AREA OF AIR BUBBLES AND ACID VALUE

CUMULATIVE VALUE OF AREA OF AIR BUBBLES

CORRELATION BETWEEN CUMULATIVE VALUE
OF AREA OF AIR BUBBLES AND VISCOSITY

CUMULATIVE VALUE OF AREA OF AIR BUBBLES

CORRELATION BETWEEN PREDICTED VALUE
AND MEASURED VALUE OF ACID VALUE

MEASURED VALUE

PREDICTED VALUE

L1　　　　L2　　　　L3

EDIBLE OIL DETERIORATION DEGREE DETERMINATION DEVICE, EDIBLE OIL DETERIORATION DEGREE DETERMINATION SYSTEM, EDIBLE OIL DETERIORATION DEGREE DETERMINATION METHOD, EDIBLE OIL DETERIORATION DEGREE LEARNING DEVICE, AND LEARNED MODEL FOR USE IN EDIBLE OIL DETERIORATION DEGREE DETERMINATION

TECHNICAL FIELD

The present invention relates to an edible oil deterioration level determination device, an edible oil deterioration level determination system, an edible oil deterioration level determination method, an edible oil deterioration level learning device, and a learned model for use in edible oil deterioration level determination.

BACKGROUND ART

Appropriate management of the quality of edible oil used in deep-fry cooking (hereinafter, referred to as "frying oil") for cooking ingredients in heated edible oil enables the quality of deep-fried foods obtained by the deep-fry cooking to be kept. It is known that frying oil deteriorates due to the oxidation which progresses in accordance with the increase in the use time and the frequency of use for deep-fry cooking. Moreover, it is also known that deep-fry cooking using the deteriorated frying oil adversely affects the quality of the deep-fried foods thus obtained. For these problems, there is a known method for objectively determining the time to change the frying oil, in which the level of deterioration of frying oil (hereinafter, referred to as "deterioration level") is determined referring to changes in the appearance, smell, color, and the like of the frying oil and the cumulative time (cumulative period of time) of use of the frying oil.

However, the conventional method of determining the deterioration level often depends on the experience (subjectivity) of a person in charge of determining the time to change the frying oil (mainly, a user who uses the frying oil). As a method of objectively determining the deterioration level of frying oil without depending on the subjectivity, for example, Patent Literature 1 discloses a method of detecting the amount of air bubbles (surface air bubbles) formed on the surface of frying oil during deep-fry cooking, preferably by means of the illuminance, to detect the deterioration level of the quality of the frying oil using the degree of the change thereof as an indicator.

CITATION LIST

Patent Literature

Patent Literature 1: JP-H-08-182624

SUMMARY OF INVENTION

Technical Problem

Among the surface air bubbles formed on the surface of frying oil during deep-fry cooking, some air bubbles are more likely to appear as the frying oil deteriorates. That is, the amount and frequency of formation (degree of formation) of the characteristic air bubbles changes depending on the deterioration of the frying oil. Accordingly, it is considered that determination of the deterioration level of oil can be made based on the degree of formation of the characteristic air bubbles. However, the method according to Patent Literature 1 in which the detection of the deterioration level is made based on merely the illuminance of the surface of the frying oil hardly distinguishes the types of the surface air bubbles of the frying oil. Thus, conventionally, it has been difficult to accurately determine the deterioration level of the frying oil considering the types of the surface air bubbles.

Therefore, an object of the present invention is to provide an edible oil deterioration level determination device, an edible oil deterioration level determination system, an edible oil deterioration level determination method, an edible oil deterioration level learning device, and a learned model for use in edible oil deterioration level determination, which enable the types of surface air bubbles of frying oil to be accurately distinguished and thus the deterioration level of the frying oil to be accurately determined.

Solution to Problem

In order to achieve the object described above, the present invention provides an edible oil deterioration level determination device for determining a deterioration level of an edible oil, comprising: an oil image acquisition section configured to acquire an oil image that is an image of the edible oil; a filter processing section configured to apply filter processing to the oil image acquired by the oil image acquisition section, the filter processing being carried out for identifying a feature area that is an area of predetermined air bubbles characterizing deterioration of the edible oil based on a range of a color of air bubbles included in the oil image; a feature parameter calculation section configured to calculate a feature parameter that is a parameter characterizing the deterioration of the edible oil in the feature area identified by the filter processing section; a deterioration indicator estimation section configured to estimate a deterioration indicator of the edible oil based on the feature parameter calculated by the feature parameter calculation section; and a deterioration level determination section configured to determine the deterioration level of the edible oil based on the deterioration indicator estimated by the deterioration indicator estimation section.

Advantageous Effects of Invention

According to the present invention, it is possible to accurately distinguish the types of surface air bubbles of frying oil, and thus accurately determine the deterioration level of the frying oil. The problems, configurations, and advantageous effects other than those described above will be clarified by explanation of the embodiments below.

DESCRIPTION OF EMBODIMENTS

An edible oil deterioration level determination system according to each embodiment of the present invention is a system for determining the deterioration level of edible oil used for cooking of deep-fried foods such as fried chickens, croquettes, French fries, and the like. In the following, cooking of deep-fried foods is referred to as "deep-fry cooking" and cooking oil used for deep-fry cooking is referred to as "frying oil".

(Arrangement in Cooking Area 1)

Firstly, an example of arrangement in a cooking area 1, which is assumed as an environment in which deep-fry cooking is performed, will be described with reference to FIG. 1.

Figure 1:
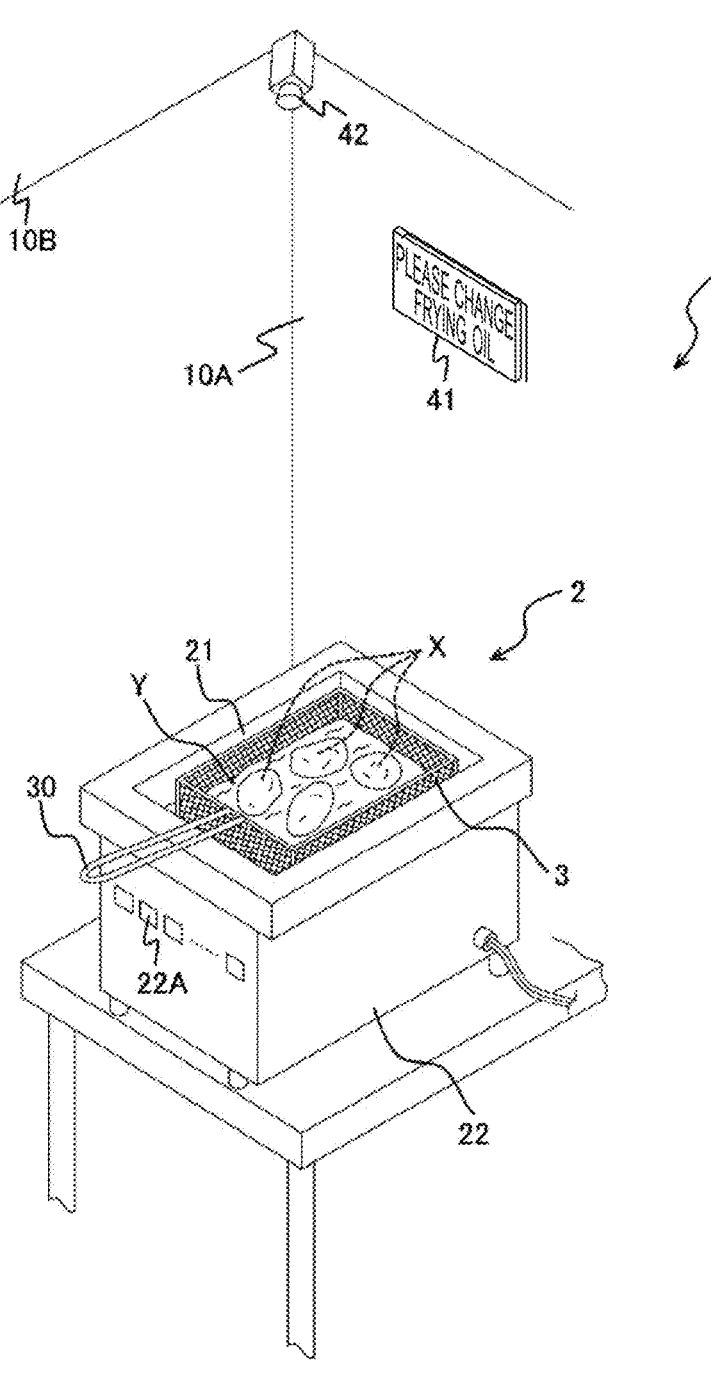
FIG. 1 illustrates an example of arrangement in a cooking area where deep-fry cooking is performed.

FIG. 1 illustrates an example of the arrangement in the cooking area 1 where deep-fry cooking is performed.

The cooking area 1 is built in stores and shops such as a convenience store or a supermarket. The cooking area 1 is provided with a tool in which deep-fry cooking is performed so as to produce a deep-fried food X to be sold to customers, which is, for example, an electric fryer 2. The fryer 2 includes an oil vat 21 for holding frying oil Y therein, and a housing 22 for accommodating the oil vat 21. On a side surface of the housing 22, a plurality of switches 22A serving as a setting operation section for setting the temperature of the frying oil Y and the details of the deep-fry cooking is provided for each type of the deep-fried food X.

In order to deep-fry the foods, firstly, a cook places the deep-fried food X before deep-fried in a fry basket 3 having a handle 30, and then hooks the handle 30 on the upper end portion of the housing 22 so that the deep-fried food X before deep-fried in the fry basket 3 is immersed in the frying oil Y. At the same time or around the same time, the cook operates one of the switches 22A which corresponds to the type of the deep-fried food X in cooking.

Subsequently, the fryer 2 identifies the one of the switches 22A which was manipulated by the cook, and when a period of time for completion of deep-fry cooking, which is associated with the manipulated one of the switches 22A, elapses, the fryer 2 notifies the cook of the completion of frying. At the same time, the fry basket 3 holding the deep-fried food X automatically rises from the oil vat 21 so that the deep-fried food X is pulled up from the state of being immersed in the frying oil. As a method of informing the completion of deep-fry cooking of the deep-fried food X, for example, a method of outputting a buzzer sound from a speaker of the fryer 2 or a method of displaying the information on a monitor 41 installed on a wall 10A near the fryer 2 may be employed. That is, each of the speaker and the monitor 41 is one of the aspects of a notification device.

The cook who is aware of the completion of deep-fry cooking of the deep-fried food X pulls up the fry basket 3 to take the deep-fried food X out therefrom. Note that pulling up the fry basket 3 out from the oil vat 21 may be automatically performed by a drive mechanism which can be provided in the fryer 2.

In the cooking area 1, a video camera 42 serving as an image capturing device for acquiring an oil surface image which is an image of the surface of the frying oil Y in the oil vat 21 is attached to a ceiling 10B above the oil vat 21. The video camera 42 is installed with its angle of view and focus being adjusted so that an image of the surface of the frying oil Y in the oil vat 21 can be continuously captured as an image of the surface of the frying oil Y in the oil vat 21.

Note that the video camera 42 does not necessarily have to be attached to the ceiling 10B. The video camera 42 may be attached to, for example, the wall 10A as long as it is held at the position allowing the oil surface image to be captured. Furthermore, the oil surface image captured by the video camera 42 may include an image of something other than the surface of the frying oil Y, such as a part of the equipment of the oil vat 21 or a material immersed in the frying oil Y (specifically, fried food X which is the object to be deep-fried, or a part of the fry basket 3).

The video camera 42 may be capable of at least capturing an oil image which is the image of the frying oil Y. Furthermore, the image capturing device does not necessarily have to be the video camera 42 for capturing a movie, but may be, for example, a still camera for capturing a still image. In the case of using a still camera, it may be configured to automatically capture an oil surface image intermittently at predetermined time intervals.

(Correlation Between Deterioration of Frying Oil Y and Deterioration Indicator)

Here, the correlation between the deterioration of the frying oil Y and each indicator of deterioration will be described with reference to FIG. 2 to FIG. 8. In the following, an example of the frying oil Y which has just been changed and thus has not been deteriorated may be referred to as "fresh frying oil Y1", while the frying oil Y that is repeatedly used and thus is deteriorated may be referred to as "deteriorated frying oil Y2".

Figure 2A:
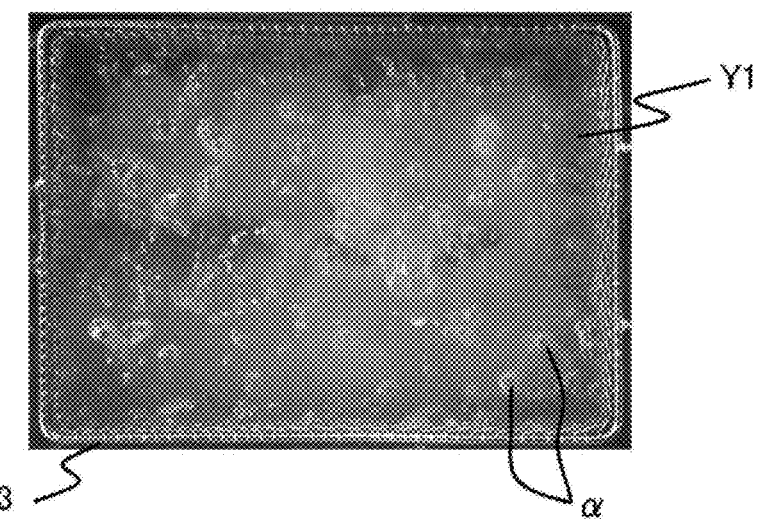
FIG. 2A illustrates a state in which a deep-fried food is being fried in fresh frying oil.
Figure 2B:
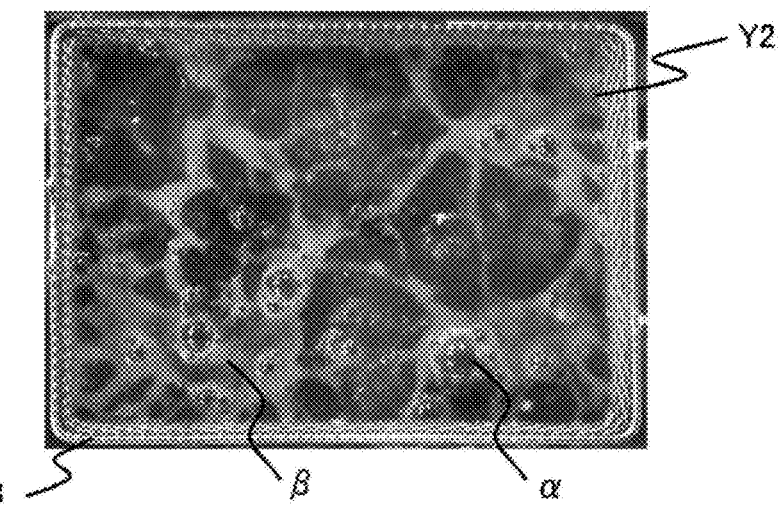
FIG. 2B illustrates a state in which a deep-fried food is being fried in deteriorated frying oil.

FIG. 2A and FIG. 2B illustrate examples of oil surface images obtained when the fry basket 3 is imaged from above the fry basket 3 during deep-fry cooking. FIG. 2A illustrates a state in which the deep-fried food X is being fried in the fresh frying oil Y1, and FIG. 2B illustrates a state in which the deep-fried food X is being fried in the deteriorated frying oil Y2.

As illustrated in FIG. 2A and FIG. 2B, during deep-fry cooking, a plurality of air bubbles (surface air bubbles) rises to the surface of the frying oil Y. These air bubbles include a plurality of types of air bubbles. For example, they include an air bubble having a relatively large diameter (hereinafter, referred to as "large air bubble(s) α") and an air bubble having a relatively small diameter (hereinafter, referred to as "fine air bubble(s) @"). The diameter R of the large air bubble α is, for example, equal to or more than 2.5 mm, and they appear in both FIG. 2A and FIG. 2B. On the other hand, the diameter R of the fine air bubble β is of, for example, less than 2.5 mm, and they appear in FIG. 2B more than in FIG. 2A.

In the following, it is assumed that two types of air bubbles (surface air bubbles) are distinguished by the size of the diameter R thereof. The numerical value of the diameter R used to define the large air bubbles α and fine air bubbles β is merely an example, and the diameter R may take a numerical value different from that as described above as long as it allows the level of deterioration of the frying oil Y to be determined focusing on the "degree of formation of air bubbles" including the amount and frequency of formation of air bubbles of different sizes.

The large air bubbles α are likely to stay in their positions on the surface of the oil where they are formed, while fine air bubbles β are likely to flow over the surface of the oil, and several of them gathers and forms a stream on the oil surface. In addition, as the frying oil Y deteriorates, the color of the frying oil Y darkens. This makes it more difficult to see the contour of the deep-fried food X in the deteriorated frying oil Y2 compared to the fresh frying oil Y1. Accordingly, using the level of visibility of the contour of the deep-fried food X as an indicator enables detection of the deterioration level of the frying oil Y2. In this case, the "difference" between the color of the deteriorated frying oil Y2 and the color of the area of the deep-fried food X is detected from the surface image of the deteriorated frying oil Y2. Note that it is also possible to estimate the deterioration level by detecting the "difference" between the color of the fresh frying oil Y1 and the color of the area of the deep-fried food X from the surface image of the fresh frying oil Y1 in advance and comparing both the "difference in color".

The major indicators (deterioration indicators) of deterioration of the frying oil Y are mainly as follows. They include, for example, the viscosity of the frying oil Y, a rate of increase in viscosity, the acid value (AV) of the frying oil Y, the color of the frying oil Y, the Anisidine value of the frying oil Y, the quantity of polar compounds of the frying oil Y, the Carbonyl value of the frying oil Y, the smoke point of the frying oil Y, the tocopherol content of the frying oil Y, the iodine value of the frying oil Y, a refractive indicator of the frying oil Y, the quantity of volatile compounds of the frying oil Y, the composition of volatile compounds of the frying oil Y, the flavor of the frying oil Y, the quantity of volatile compounds of the deep-fried food X obtained by deep-fry cooking with the frying oil Y, the composition of volatile compounds of the deep-fried food X obtained by deep-fry cooking with the frying oil Y, and the flavor of the deep-fried food X obtained by deep-fry cooking with the frying oil Y. Selecting and using one or more deterioration indicators from among these deterioration indicators above enables detection of the deterioration of the frying oil Y.

For example, an increase rate of viscosity is a value calculated as a ratio of increase in the viscosity relative to the viscosity (viscosity at the start of use) measured before the deep-fried food X is fried for the first time in the fresh frying oil Y just after being changed. Note that the viscosity is a value which can be measured by an available viscometer, for example, an E-type viscometer (TVE-25H, made by Toki Sangyo Co., Ltd.).

Furthermore, for example, the acid value is a value measured by a method according to the standard methods for the analysis of fats, oils and related materials, 2.3.1-2013. The color is a value of (Y+10R) measured by a method according to the standard methods for the analysis of fats, oils and related materials, 2.2.1.1-2013. The Anisidine value is a value measured by a method according to the standard methods for the analysis of fats, oils and related materials, 2.5.3-2013. The quantity of polar compounds is a value measured by a method according to the standard methods for the analysis of fats, oils and related materials, 2.5.5-2013 and an available instrument for measuring polar compounds (for example, made by Testo K. K.) based thereon.

Still further, the volatile compounds are compounds (odor components) that volatilize from the deep-fried food X and the frying oil Y, and the quantity and composition of the compounds change as the frying oil Y deteriorates. The volatile compounds are measured by a gas chromatograph-mass spectrometer (GC-MS), an odor sensor, or the like. In order to measure the flavor, a sensory evaluation (evaluation method involving the use of human senses by actually tasting) or a taste sensor are used. That is, the deterioration indicators of the frying oil Y include not only chemical deterioration indicators but also deterioration indicators in terms of taste.

As illustrated in FIG. 3 to FIG. 8, the degree of formation of air bubbles on the surface of the frying oil Y during deep-fry cooking correlates with the deterioration level of the frying oil Y. In particular, a strong correlation between the degree of formation of the "fine air bubbles β" and the deterioration level of the frying oil Y can be observed therefrom.

FIG. 3 to FIG. 5 illustrate examples of the correlations, each of which is between a ratio of the area (area ratio) of an area where air bubbles are formed (air bubble area) relative the total area in the oil surface image, which corresponds to the degree of formation of air bubbles, and a part of the deterioration indicators listed above. FIG. 6 to FIG. 8 illustrate examples of the correlations, each of which is between the number of air bubbles (regardless of the type of air bubbles) formed on the surface of the frying oil Y, which is identified from the oil surface image, and a part of the deterioration indicators. The correlation analysis illustrated in FIG. 3 to FIG. 8 is based on the analysis performed by, in the case of deep-frying four fried chickens to be deep-fried in the fryer 2 for 0-9 days, using the mean value of n=3 and dividing the mean value by 4 to convert it to a value per fried chicken.

Figure 3A:
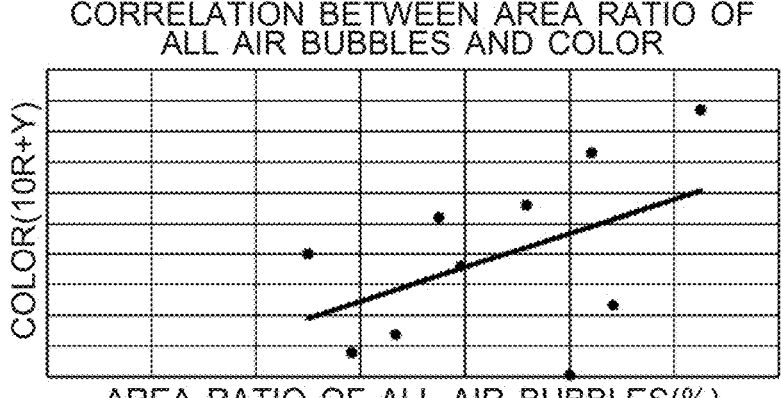
FIG. 3A is a graph illustrating a correlation between the area ratio of all air bubbles formed on a surface of frying oil and the color of the frying oil.
Figure 3B:
FIG. 3B is a graph illustrating a correlation between the area ratio of large air bubbles among air bubbles formed on a surface of frying oil and the color of the frying oil.
Figure 3B:
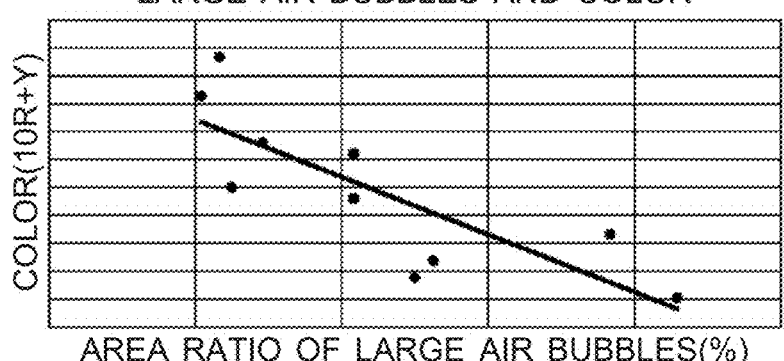
Figure 3C:
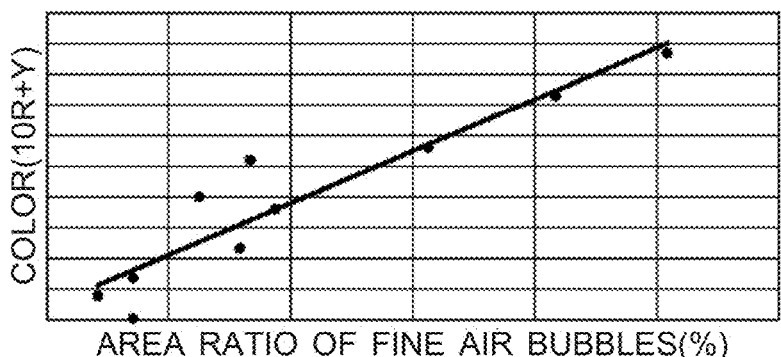
FIG. 3C is a graph illustrating a correlation between the area ratio of fine air bubbles among air bubbles formed on a surface of frying oil and the color of the frying oil.

FIG. 3A illustrates a correlation between the area ratio of all air bubbles formed on the surface of the frying oil Y and the color of the frying oil Y, FIG. 3B illustrates a correlation between the area ratio of the large air bubbles among the air bubbles formed on the surface of the frying oil Y and the color of the frying oil Y, and FIG. 3C illustrates a correlation between the area ratio of the fine air bubbles among the air bubbles formed on the surface of the frying oil Y and the color of the frying oil Y.

As illustrated in FIG. 3A and FIG. 3C, positive correlations are observed both between the area ratio of all the air bubbles and the color of the frying oil Y, and between the area ratio of the fine air bubbles and the color of the frying oil Y. In particular, a stronger positive correlation can be observed between the area ratio of the fine air bubbles 3 and the color of the frying oil Y. On the other hand, as illustrated in FIG. 3B, a negative correlation is observed between the area ratio of the large air bubbles α and the color of the frying oil Y.

It is known that the deterioration indicator "color" used in the exemplary graphs illustrated in FIG. 3A to FIG. 3C is positively correlated with the deterioration of the frying oil Y. Thus, in particular, estimating the color of the frying oil Y based on the area ratio of the fine air bubbles β enables precise determination of the deterioration of the frying oil Y.

Figure 4A:
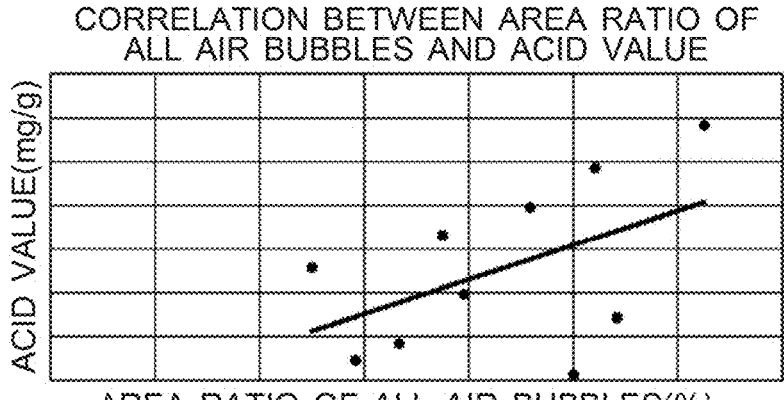
FIG. 4A is a graph illustrating a correlation between the area ratio of all air bubbles formed on a surface of frying oil and the acid value of the frying oil.
Figure 4B:
FIG. 4B is a graph illustrating a correlation between the area ratio of large air bubbles among air bubbles formed on a surface of frying oil and the acid value of the frying oil.
Figure 4B:
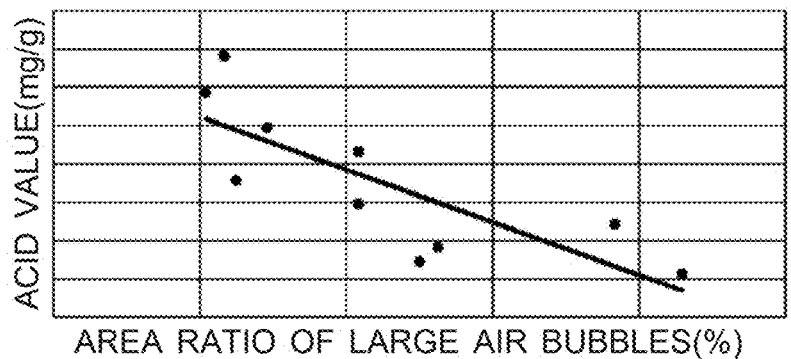
Figure 4C:
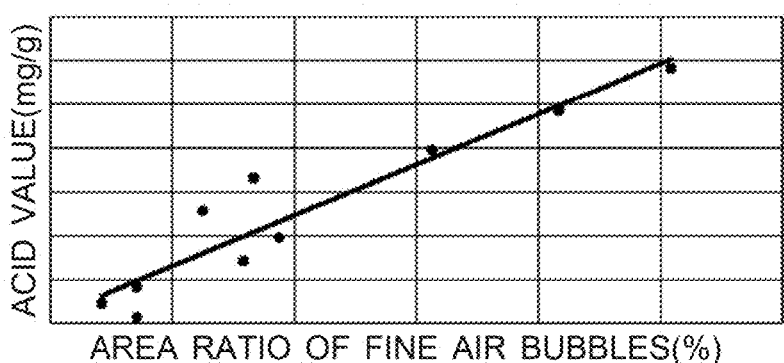
FIG. 4C is a graph illustrating a correlation between the area ratio of fine air bubbles among air bubbles formed on a surface of frying oil and the acid value of the frying oil.

FIG. 4A illustrates a correlation between the area ratio of all air bubbles formed on the surface of the frying oil Y and the acid value of the frying oil Y, FIG. 4B illustrates a correlation between the area ratio of the large air bubbles α among the air bubbles formed on the surface of the frying oil Y and the acid value of the frying oil Y, and FIG. 4C illustrates a correlation between the area ratio of the fine air bubbles β among the air bubbles formed on the surface of the frying oil Y and the acid value of the frying oil Y.

As illustrated in FIG. 4A and FIG. 4C, positive correlations are observed both between the area ratio of all the air bubbles and the acid value of the frying oil Y, and between the area ratio of the fine air bubbles β and the acid value of the frying oil Y. In particular, a stronger positive correlation can be observed between the area ratio of the fine air bubbles β and the acid value of the frying oil Y. On the other hand, as illustrated in FIG. 4B, a negative correlation is observed between the area ratio of the large air bubbles α and the acid value.

It is known that the deterioration indicator "acid value" used in the exemplary graphs illustrated in FIG. 4A to FIG. 4C is positively correlated with the deterioration of the frying oil Y. Thus, in particular, estimating the acid value of the frying oil Y based on the area ratio of the fine air bubbles β enables precise determination of the deterioration of the frying oil Y.

Figure 5A:
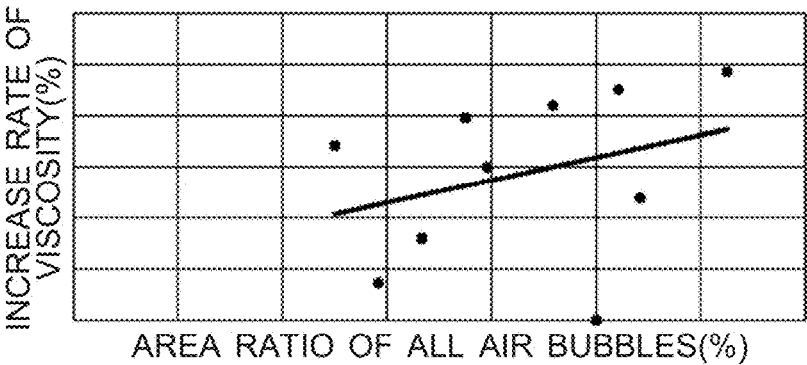
FIG. 5A is a graph illustrating a correlation between the area ratio of all air bubbles formed on a surface of frying oil and an increase rate of viscosity of frying oil.
Figure 5B:
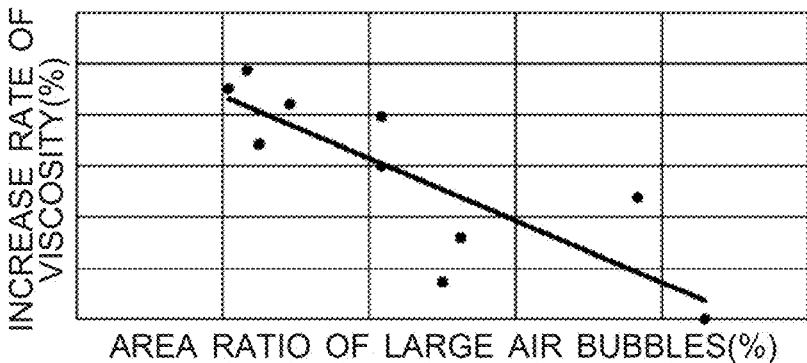
FIG. 5B is a graph illustrating a correlation between the area ratio of large air bubbles among air bubbles formed on a surface of frying oil and an increase rate of viscosity of frying oil.
Figure 5C:
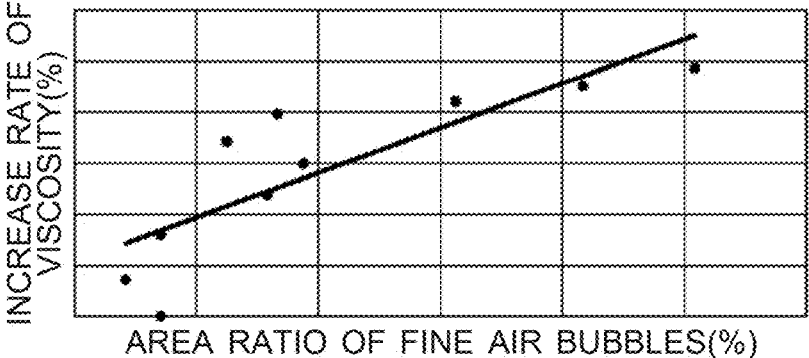
FIG. 5C is a graph illustrating a correlation between the area ratio of fine air bubbles among air bubbles formed on a surface of frying oil and an increase rate of viscosity of frying oil.

FIG. 5A illustrates a correlation between the area ratio of all air bubbles formed on the surface of the frying oil Y and the increase rate of viscosity of the frying oil Y, FIG. 5B illustrates a correlation between the area ratio of the large air bubbles among the air bubbles formed on the surface of the frying oil Y and the increase rate of viscosity of the frying oil Y, and FIG. 5C illustrates a correlation between the area ratio of the fine air bubbles among the air bubbles formed on the surface of the frying oil Y and the increase rate of viscosity of the frying oil Y.

As illustrated in FIG. 5A and FIG. 5C, positive correlations are observed both between the area ratio of all the air bubbles and the increase rate of viscosity of the frying oil Y, and between the area ratio of the fine air bubbles β and the increase rate of viscosity of the frying oil Y. In particular, a stronger positive correlation can be observed between the area ratio of the fine air bubbles β and the increase rate of viscosity of the frying oil Y. On the other hand, as illustrated in FIG. 5B, a negative correlation is observed between the area ratio of the large air bubbles α and the increase ratio of viscosity of the frying oil Y.

It is known that the deterioration indicator "increase rate of viscosity" used in the exemplary graphs illustrated in FIG. 5A to FIG. 5C is positively correlated with the deterioration of the frying oil Y. Thus, in particular, estimating the increase rate of viscosity of the frying oil Y based on the area ratio of the fine air bubbles β enables precise determination of the deterioration of the frying oil Y.

Figure 6A:
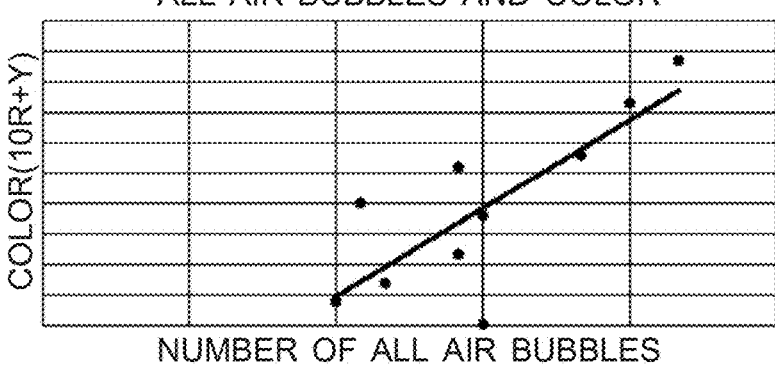
FIG. 6A is a graph illustrating a correlation between the number of all air bubbles formed on a surface of frying oil and the color of frying oil.
Figure 6B:
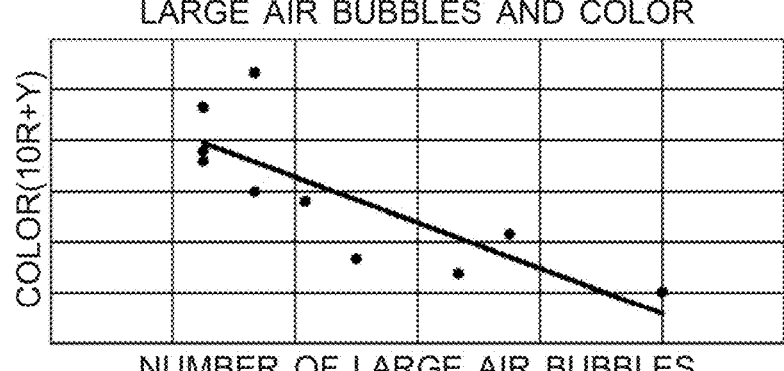
FIG. 6B is a graph illustrating a correlation between the number of large air bubbles among air bubbles formed on a surface of frying oil and the color of frying oil.
Figure 6C:
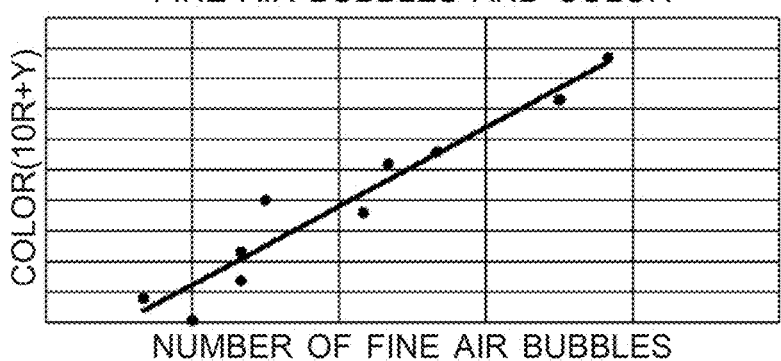
FIG. 6C is a graph illustrating a correlation between the number of fine air bubbles among air bubbles formed on a surface of frying oil and the color of frying oil.

FIG. 6A illustrates a correlation between the number of all air bubbles formed on the surface of the frying oil Y and the color of the frying oil Y, FIG. 6B illustrates a correlation between the number of large air bubbles α among the air bubbles formed on the surface of the frying oil Y and the color of the frying oil Y, and FIG. 6C illustrates a correlation between the number of fine air bubbles β among the air bubbles formed on the surface of the frying oil Y and the color of the frying oil Y.

As illustrated in FIG. 6A and FIG. 6C, positive correlations are observed both between the number of all the air bubbles and the color of the frying oil Y, and between the number of fine air bubbles β and the color of the frying oil Y. In particular, a stronger positive correlation can be observed between the number of fine air bubbles β and the color of the frying oil Y. On the other hand, as illustrated in FIG. 6B, a negative correlation is observed between the number of large air bubbles α and the color of the frying oil Y.

It is known that the deterioration indicator "color" used in the exemplary graphs illustrated in FIG. 6A to FIG. 6C is positively correlated with the deterioration of the frying oil Y. Thus, in particular, estimating the color of the frying oil Y based on the number of fine air bubbles β enables precise determination of the deterioration of the frying oil Y.

Figure 7A:
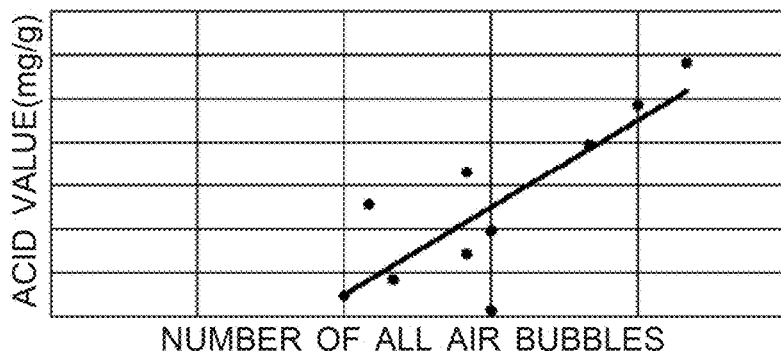
FIG. 7A is a graph illustrating a correlation between the number of all air bubbles formed on a surface of frying oil and the acid value of frying oil.
Figure 7B:
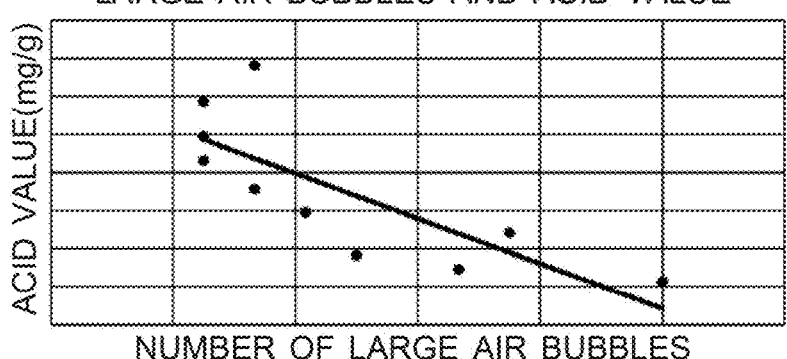
FIG. 7B is a graph illustrating a correlation between the number of large air bubbles among air bubbles formed on a surface of frying oil and the acid value of frying oil.
Figure 7C:
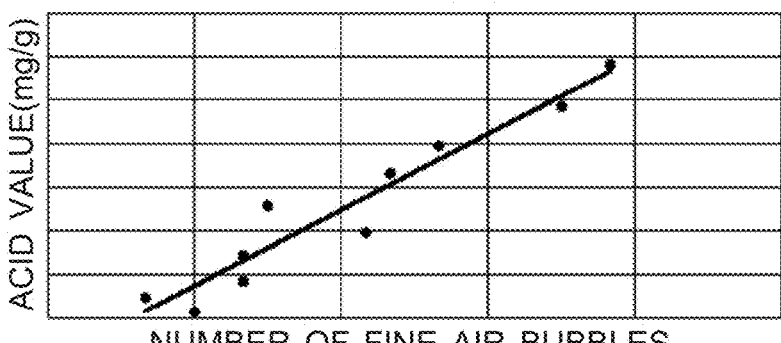
FIG. 7C is a graph illustrating a correlation between the number of fine air bubbles among air bubbles formed on a surface of frying oil and the acid value of frying oil.

FIG. 7A illustrates a correlation between the number of all air bubbles formed on the surface of the frying oil Y and the acid value of the frying oil Y, FIG. 7B illustrates a correlation between the number of large air bubbles among the air bubbles formed on the surface of the frying oil Y and the acid value of the frying oil Y, and FIG. 7C illustrates a correlation between the number of fine air bubbles among the air bubbles formed on the surface of the frying oil Y and the acid value of the frying oil Y.

As illustrated in FIG. 7A and FIG. 7C, positive correlations are observed both between the number of all the air bubbles and the acid value of the frying oil Y, and between the number of fine air bubbles β and the acid value of the frying oil Y. In particular, a stronger positive correlation can be observed between the number of fine air bubbles β and the acid value of the frying oil Y. On the other hand, as illustrated in FIG. 7B, a negative correlation is observed between the number of large air bubbles α and the acid value of the frying oil Y.

It is known that the deterioration indicator "acid value" used in the exemplary graphs illustrated in FIG. 7A to FIG. 7C is positively correlated with the deterioration of the frying oil Y. Thus, in particular, estimating the acid value of the frying oil Y based on the number of fine air bubbles β enables precise determination of the deterioration of the frying oil Y.

Figure 8A:
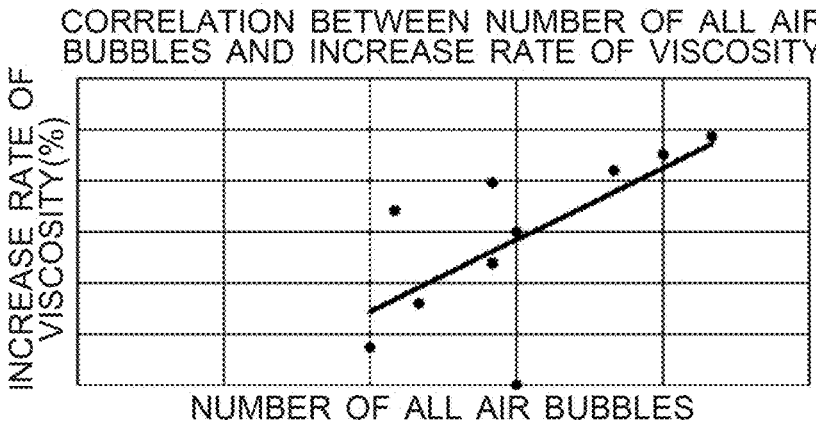
FIG. 8A is a graph illustrating a correlation between the number of all air bubbles formed on a surface of frying oil and an increase rate of viscosity of frying oil.
Figure 8B:
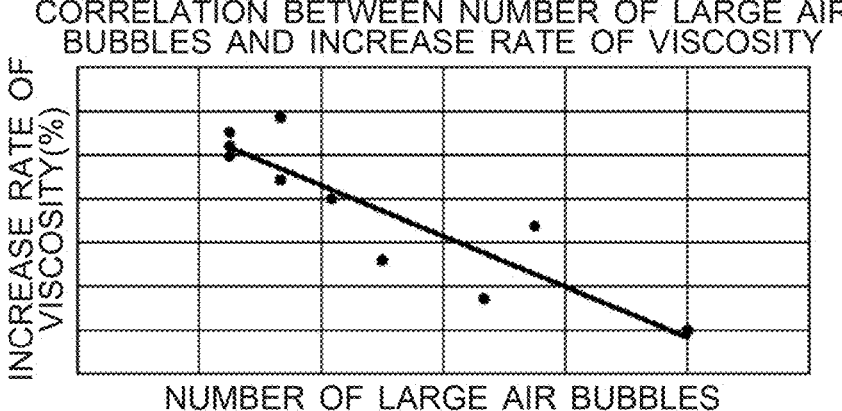
FIG. 8B is a graph illustrating a correlation between the number of large air bubbles formed on a surface of frying oil and an increase rate of viscosity of frying oil.
Figure 8C:
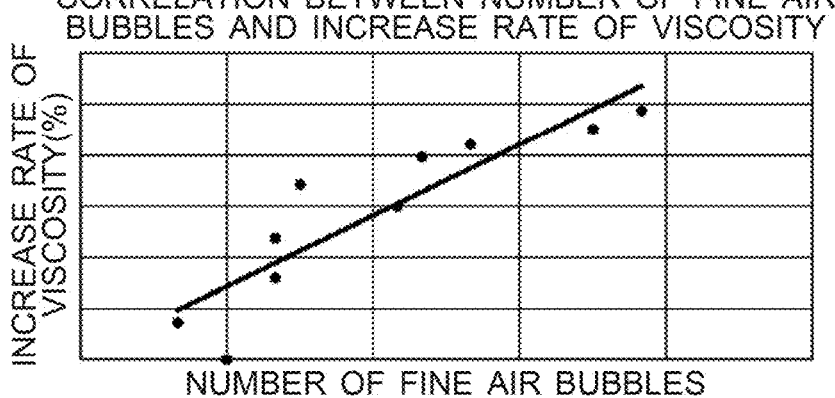
FIG. 8C is a graph illustrating a correlation between the number of fine air bubbles formed on a surface of frying oil and an increase rate of viscosity of frying oil.

FIG. 8A illustrates a correlation between the number of all air bubbles formed on the surface of the frying oil Y and the increase rate of viscosity of the frying oil Y, FIG. 8B illustrates a correlation between the number of large air bubbles α among the air bubbles formed on the surface of the frying oil Y and the increase rate of viscosity of the frying oil Y, and FIG. 8C illustrates a correlation between the number of fine air bubbles among the air bubbles formed on the surface of the frying oil Y and the increase rate of viscosity of the frying oil Y.

As illustrated in FIG. 8A and FIG. 8C, positive correlations are observed both between the number of all the air bubbles and the increase rate of viscosity of the frying oil Y, and between the number of fine air bubbles β and the increase rate of viscosity of the frying oil Y. In particular, a stronger positive correlation can be observed between the number of fine air bubbles β and the increase rate of viscosity of the frying oil Y. On the other hand, as illustrated in FIG. 8B, a negative correlation is observed between the number of large air bubbles α and the increase rate of viscosity of the frying oil Y.

It is known that the deterioration indicator "increase rate of viscosity" used in the exemplary graphs illustrated in FIG. 8A to FIG. 8C is positively correlated with the deterioration of the frying oil Y. Thus, in particular, estimating the increase rate of viscosity of the frying oil Y based on the number of fine air bubbles β enables precise determination of the deterioration of the frying oil Y.

As described above, it can be observed that the fine air bubbles β among all air bubbles formed on the surface of the frying oil Y are correlated with the deterioration indicators more strongly than all the air bubbles and the large air bubbles α (see FIG. 3C, FIG. 4C, FIG. 5C, FIG. 6C, FIG. 7C, and FIG. 8C). Therefore, in order to determine the deterioration of the frying oil Y precisely, it is desirable to focus on the fine air bubbles β more than all the air bubbles or the large air bubbles α. In other words, fine air bubbles β correspond to "predetermined air bubbles" that characterize the level of deterioration (progress of deterioration) of the frying oil Y.

Furthermore, the area ratio and number of fine air bubbles β correspond to variables that vary in accordance with the level of deterioration of the frying oil Y. That is, it can be said that the data obtained by identifying the formation of the fine air bubbles β is a feature parameter that characterizes the level of deterioration (progress of deterioration) of the frying oil Y. In addition to the area ratio and the number of the fine air bubbles β, the feature parameters include one or more indicators selected from the speed of disappearance of air bubbles, the presence or absence of a stream of the fine air bubbles β, the difference between the color of the frying oil Y and the color of the area of the deep-fried food X (visibility level of the contour of the deep-fried food X), and a cumulative value of the area of air bubbles. Hereinafter, a deterioration level determination device 5 for determining the deterioration level of the frying oil Y will be described for each embodiment.

First Embodiment

The deterioration level determination device 5 according to a first embodiment of the present invention will be described with reference to FIG. 9 to FIG. 24.

(Configuration of Deterioration Level Determination Device 5)

A configuration of the deterioration level determination device 5 will be described with reference to FIG. 9 to FIG. 17.

Figure 9:
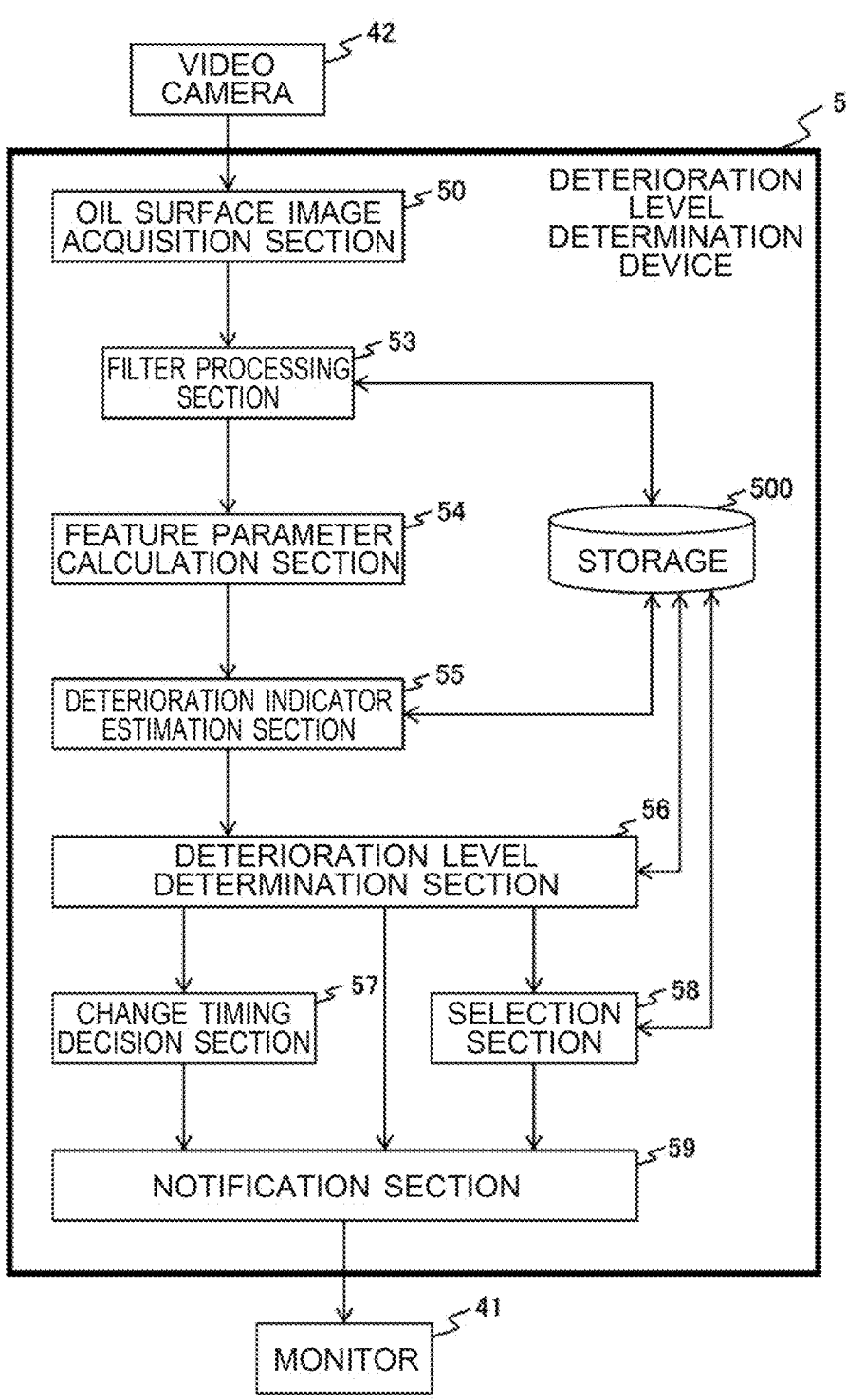
FIG. 9 is a functional block diagram illustrating functions of a deterioration level determination device according to the first embodiment.

FIG. 9 is a functional block diagram illustrating functions of the deterioration level determination device 5 according to the first embodiment.

The deterioration level determination device 5 has a function to receive, as input data, an oil surface image which is an image of the surface of the frying oil Y directly from the video camera 42 or indirectly via an external storage medium, further or from a remote location via a communication line, and output, as output data, a result of determination of the deterioration level of the frying oil Y. Furthermore, the deterioration level determination device 5 has a function to notify the outside, such as a user, of the determination result.

As in the case of general computers, the deterioration level determination device 5 includes, as hardware resources, a hardware configuration in which a CPU, a RAM, a ROM, an HDD, an input I/F, and an output I/F are connected to each other via a bus. The oil surface image is input via the input I/F as the image data acquired by the image capturing device such as the video camera 42. The oil surface image which has been input is displayed via an image display means such as the monitor 41 connected to the output I/F.

In this hardware configuration, the CPU reads a control program (software) stored in a recording medium such as the ROM, the HDD, or an optical disc and loads it on the RAM so as to execute the loaded control program, whereby each function of the deterioration level determination device 5 can be implemented by the cooperation of the control program and the hardware resources.

Note that, in the present embodiment, the deterioration level determination device 5 is described as a computer composed of a combination of software and hardware, however, the present invention is not limited thereto. As one of the examples of configurations of other computers, an integrated circuit for implementing functions of a control program executed at the fryer 2 side may be used.

The deterioration level determination device 5 includes an oil surface image acquisition section 50, an air bubble image extraction section 51, an air bubble dimension calculation section 52, a feature area identification section 53, a feature parameter calculation section 54, a deterioration indicator estimation section 55, a deterioration level determination section 56, a change timing decision section 57, a selection section 58, a notification section 59, and a storage 500.

The oil surface image acquisition section 50 corresponds to an oil image acquisition section, and is configured to acquire data (oil surface image data) about an image of the surface of the frying oil Y (oil surface image) as an image of the frying oil Y (oil image) based on an image of the fry basket 3 captured by the video camera 42.

For example, in the case that the image of the fry basket 3 to be input is a still image, the oil surface image acquisition section 50 extracts the contour of the fry basket 3 and acquires only the inside of the contour so as to obtain the oil surface image to be processed. In the case that the image of the fry basket 3 is a movie, the oil surface image acquisition section 50 decomposes the moving image into frames composing the movie (for example, if it is a movie of 30 fps, decomposes it into images every $\frac{1}{30}$ second), and extract the contour of the fry basket 3 included in each frame so as to acquire only the inside of the contour as the oil surface image.

Alternatively, the oil surface image acquisition section 50 may carry out the image processing of excluding the color (for example, color in the range of HSV=(120, 0, 80) to (175, 20, 140)) of a portion other than the frying oil Y, such as the frying basket 3, to acquire only the frying oil Y inside the contour of the frying basket 3 as the oil surface image data. For the image processing of excluding a particular color range, for example, OpenCV (Open Source Computer Vision Library), which is an open source computer vision library developed and published by Intel Corporation, may be used.

The filter processing section 53 applies the filter processing to the oil surface image acquired by the oil surface image acquisition section 50. In this filter processing, an area including the fine air bubbles β is identified as a feature area based on the color of an air bubble portion included in the oil surface image.

The color of the air bubble portion is not always a single color, but is defined by the hue (H), saturation (S), lightness (V), and the like, and includes variation. Accordingly, the filter processing section 53 defines a range of the numerical values of which the hue (H), saturation (S), and lightness (V) of the image of the air bubble portion can take so that the color of the air bubble portion included in the oil surface image can be identified as a numerical value range, and sets it as an "air bubble color range". Then, the filter processing section 53 executes the filter processing based on the air bubble color range. That is, within the "area including the fine air bubbles β" corresponding to a partial area of the air bubbles included in the whole area of the oil surface image, the feature area corresponds to further a portion thereof (an area included in the color range).

The filter processing executed by the filter processing section 53 is the one in which a plurality of types of filter processing are combined. For example, the filter processing section 53 executes the filter processing including first filter processing and second filter processing.

Specifically, in the first filter processing, the filter processing section 53 carries out the processing using a first threshold range ThR1 on the oil surface image acquired by the oil surface image acquisition section 50. Hereinafter, carrying out the first filter processing may be referred to as "applying the first filter". The "first threshold range ThR1" is set to a specific color range (specifically, a range defined by the hue (H), saturation (S), and lightness (V)) allowing, from among the fine air bubbles β included in the oil surface image, the fine air bubbles β which is a portion thereof to be extracted.

In the second filter processing, the filter processing section 53 carries out the processing using a second threshold range ThR2 on the oil surface image acquired by the oil surface image acquisition section 50. Hereinafter, carrying out the second filter processing may be referred to as "applying the second filter". The "second threshold range ThR2" is set to a specific color range (in the present embodiment, a range of the saturation (S)) broader than first threshold range ThR1.

That is, the filter processing section 53 executes the image filter processing using two different color threshold ranges (ranges in which the mask processing is carried out). The second threshold range ThR2 is set to the range that is broader than the first threshold range ThR1. Accordingly, applying the second filter to the oil surface image allows all the fine air bubbles β included in the oil surface image to be extracted.

In the first filter processing, the large air bubbles α would not be extracted from the oil surface image together with a part of the fine air bubbles β, on the other hand, in the second filter processing, in some cases, a part of the large air bubbles α may be extracted from the oil surface image together with all the fine air bubbles β.

The filter processing section 53 uses, for example, the OpenCV described above to apply the first filter to the oil surface image extracted by the oil surface image acquisition section 50 in the range of HSV=(15, 30, 135) to (20, 40, 185) set as the first threshold range ThR1. In the same manner, the filter processing section 53 uses the OpenCV to apply the second filter to the oil surface image extracted by the oil surface image acquisition section 50 in the range of HSV= (15, 30, 135) to (20, 66, 186) set as the second threshold range ThR2.

Note that the filter processing carried out by the filter processing section 53 does not necessarily have to be the filter processing using the OpenCV. There is no particular limitation on the software library to be used in the filter processing as long as the filter processing based on the color of air bubbles can be carried out. Furthermore, in the example described above, both the first threshold range ThR1 and the second threshold range ThR2 are set using the color space defined by HSV, however, they are not limited thereto but may be set using other color spaces such as the one defined by RGB.

In the present embodiment, the filter processing section 53 applies the second filter processing to the oil surface image based on the result of the first filter processing applied to the oil surface image. Specifically, firstly, the filter processing section 53 carries out the first filter processing on the oil surface image acquired by the oil surface image acquisition section 50, and then determines whether the air bubbles satisfying the first threshold range ThR1 (a part of the fine air bubbles β) have been extracted from the oil surface image by the first filter processing.

Upon determining that the air bubbles satisfying the first threshold range ThR1 have been extracted from the oil surface image acquired by the oil surface image acquisition section 50, the filter processing section 53 carries out the second filter processing on the oil surface image acquired by the oil surface image acquisition section 50 to identify the area of the air bubbles satisfying the second threshold range ThR2 extracted from the oil surface image as a specific area by the second filter processing.

On the other hand, upon determining that the air bubbles satisfying the first threshold range ThR1 have not been extracted from the oil surface image acquired by the oil surface image acquisition section 50 as a result of execution of the first filter processing, the filter processing section 53 sets the feature area to 0 (zero). In this case, the filter processing section 53 does not apply the second filter processing to the oil surface image.

That is, the first filter processing using the first threshold range ThR1 is the filter processing for determining whether the air bubbles that satisfy the first threshold range ThR1 (a part of the fine air bubbles β) are included in the oil surface image. Then, the second filter processing using the second threshold range ThR2 is carried out only when the air bubbles satisfying the first threshold range ThR1 have been extracted from the oil surface image acquired by the oil surface image acquisition section 50.

Accordingly, when the air bubbles satisfying the first threshold range ThR1 have been extracted as a result of the first filter processing applied to the oil surface image acquired by the oil surface image acquisition section 50, the filter processing section 53 applies the filter again to the oil surface image acquired by the oil surface image acquisition section 50 using the second filter.

In the present embodiment, the feature parameter calculation section 54 is configured to calculate a feature parameter F in the feature area identified by the filter processing section 53. The "feature parameter(s) F" includes information based on a plurality of numerical values. For example, the "feature parameter F" may include the "area ratio", which is a ratio of the area of the feature area including the "fine air bubble β" relative to the total area of the oil surface. The number of "fine air bubbles β" included in the feature area also corresponds to the "feature parameter F".

Furthermore, the disappearance speed (elapsed time from formation to disappearance) of each air bubble, the presence or absence of fluctuation (stream) of the positions of the "fine air bubbles s" in the oil surface within the feature area and its adjacent area, the difference between the color of the frying oil Y and the color of the area of the deep-fried food X, and a cumulative value of the area of the air bubbles also correspond to the "feature parameter F", respectively. The feature parameter calculation section 54 calculates all or a part of the plurality of "feature parameters F" listed above.

The "disappearance speed of each air bubble" corresponds to an elapsed time from formation of each air bubble on the surface of the frying oil Y during deep-fry cooking to disappearance thereof. That is, a relatively short elapsed time from formation to disappearance corresponds to the "high disappearance speed" while a relatively long elapsed time corresponds to the "low disappearance speed".

In the case of using the disappearance speed of each air bubble as the feature parameter F, since it is not limited to the disappearance speed of the fine air bubble β, the feature parameter calculation section 54 may calculate the disappearance speed of the large air bubbles α included in the oil surface image acquired by the oil surface image acquisition section 50. That is, the deterioration level determination device 5 does not necessarily have to include the air bubble dimension calculation section 52 and the feature area identification section 53.

Figure 10:
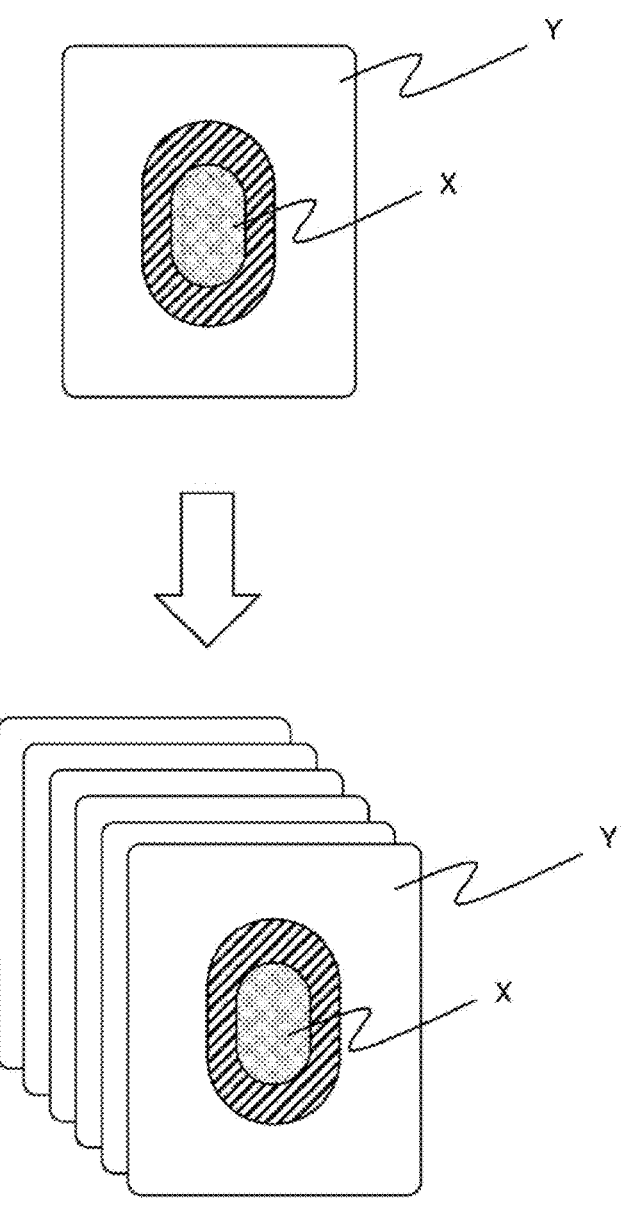
FIG. 10 is a diagram for explaining a method of calculating a cumulative value of the area of air bubbles in a deterioration level determination device according to the first embodiment.

Here, the "cumulative value of the area of air bubbles" will be described with reference to FIG. 10. FIG. 10 is a diagram for explaining a method of calculating a cumulative value of the area of air bubbles in the deterioration level determination device 5 according to the first embodiment.

As illustrated in the upper part of FIG. 10, firstly, the feature parameter calculation section 54 calculates, as the "value of the area of air bubbles", the ratio of the area (area ratio) of air bubbles (including the large air bubbles α and the fine air bubbles β) relative to the total area of the oil surface based on the oil surface image acquired by the oil surface image acquisition section 50.

Subsequently, as illustrated in the lower part of FIG. 10, the feature parameter calculation section 54 accumulates the value of the area of the air bubbles calculated over time within a predetermined period of time (for example, 30 minutes) so as to obtain the "cumulative value of the area of air bubbles".

In the same manner as the disappearance speed of each air bubble described above, in the case of using the cumulative value of the area of air bubbles as the feature parameter F, the feature parameter calculation section 54 may calculate the cumulative value of the area of all air bubbles included in the oil surface image acquired by the oil surface image acquisition section 50, may calculate the cumulative value of the area of the large air bubbles α included in the oil surface image acquired by the oil surface image acquisition section 50, or may calculate the cumulative value of the area of the fine air bubbles β identified by the filter processing section 53.

The deterioration indicator estimation section 55 is configured to estimate a deterioration indicator DI of the frying oil Y based on the feature parameter F calculated by the feature parameter calculation section 54. Specifically, the deterioration indicator estimation section 55 estimates the deterioration indicator DI corresponding to the feature parameter F in accordance with a correlation between each feature parameter F illustrated in FIG. 11 to FIG. 16 and the deterioration indicator DI. In this connection, the "color of the frying oil Y" which is the deterioration indicator DI does not necessarily matches the "color of the frying oil Y obtainable based on the oil surface image", however, the correspondence between the "color of the frying oil Y" and the "color of the frying oil Y obtainable based on the oil surface image" is stored in the storage 500 of the deterioration level determination device 5, and thus the "color of the frying oil Y obtainable based on the oil surface image" is converted to the "color of the frying oil Y" based on the correspondence.

Figure 11A:
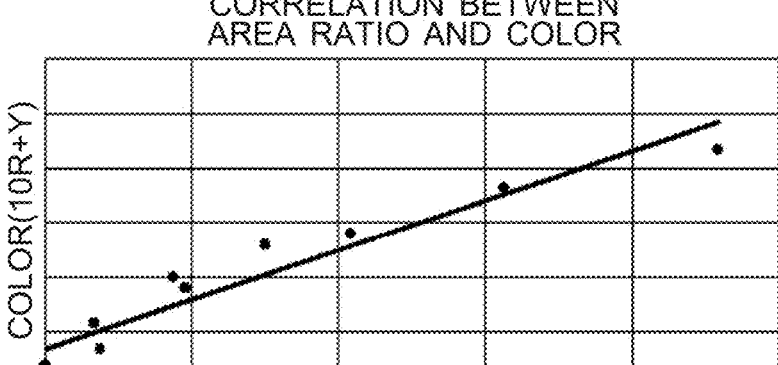
FIG. 11A is a graph illustrating a correlation between the area ratio of fine air bubbles and the color of frying oil.
Figure 11B:
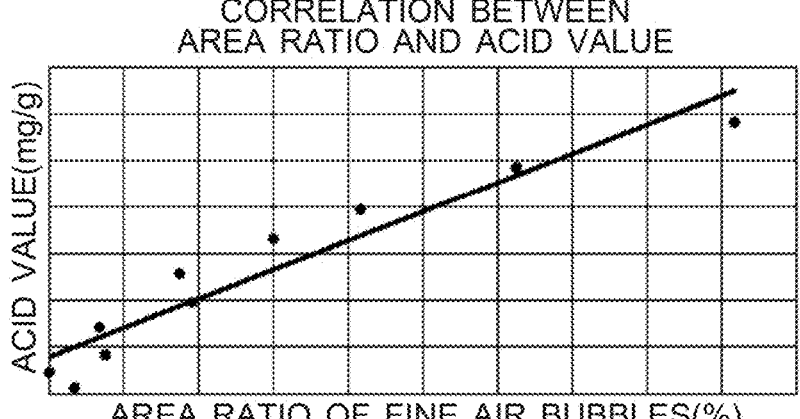
FIG. 11B is a graph illustrating a correlation between the area ratio of fine air bubbles and the acid value of frying oil.
Figure 11C:
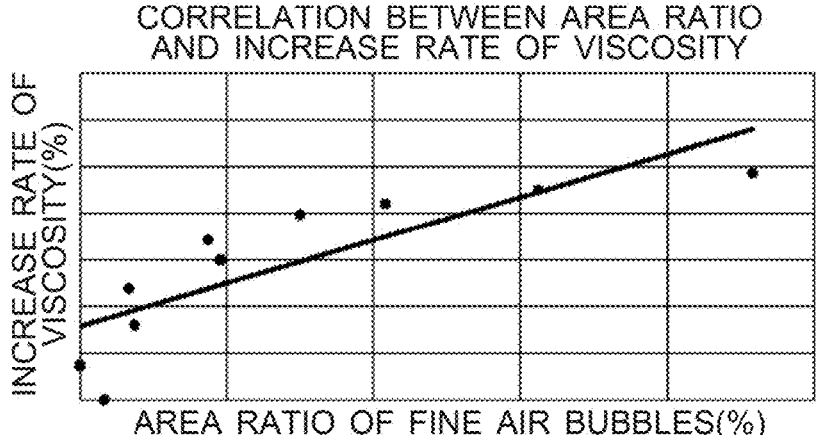
FIG. 11C is a graph illustrating a correlation between the area ratio of fine air bubbles and the increase rate of viscosity of frying oil.

FIG. 11A illustrates a correlation between the area ratio of the fine air bubbles β and the color of the frying oil Y, FIG. 11B illustrates a correlation between the area ratio of the fine air bubbles β and the acid value of the frying oil Y, and FIG. 11C illustrates a correlation between the area ratio of the fine air bubbles β and the increase rate of viscosity of the frying oil Y. Positive correlations are observed between the area ratio of the fine air bubbles β and the color of the frying oil Y, the acid value of the frying oil Y, and the increase rate of viscosity of the frying oil Y, respectively.

Figure 12A:
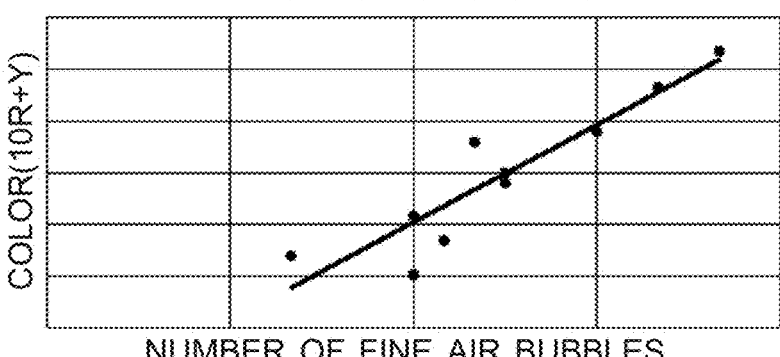
FIG. 12A is a graph illustrating a correlation between the number of fine air bubbles and the color of frying oil.
Figure 12B:
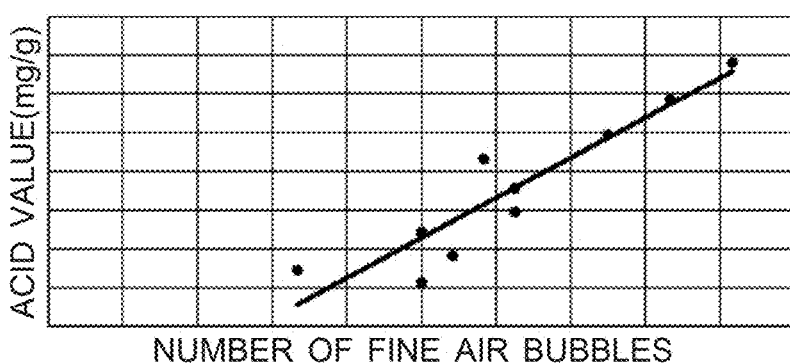
FIG. 12B is a graph illustrating a correlation between the number of fine air bubbles and the acid value of frying oil.
Figure 12C:
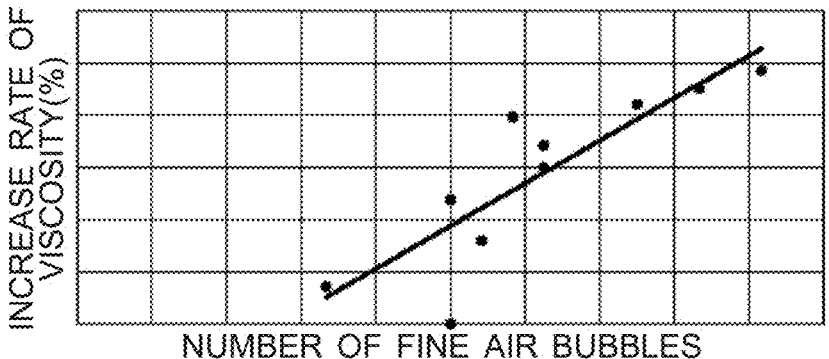
FIG. 12C is a graph illustrating a correlation between the number of fine air bubbles and the increase rate of viscosity of frying oil.

FIG. 12A illustrates a correlation between the number of fine air bubbles β and the color of the frying oil Y, FIG. 12B illustrates a correlation between the number of fine air bubbles β and the acid value of the frying oil Y, and FIG. 12C illustrates a correlation between the number of fine air bubbles β and the increase rate of viscosity of the frying oil Y. Positive correlations are observed between the number of fine air bubbles β and the color of the frying oil Y, the acid value of the frying oil Y, and the increase rate of viscosity of the frying oil Y, respectively.

Figure 13A:
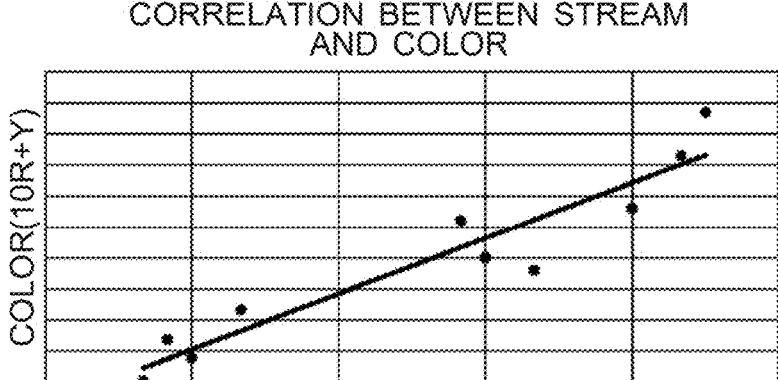
FIG. 13A is a graph illustrating a correlation between the stream of fine air bubbles and the color of frying oil.
Figure 13B:
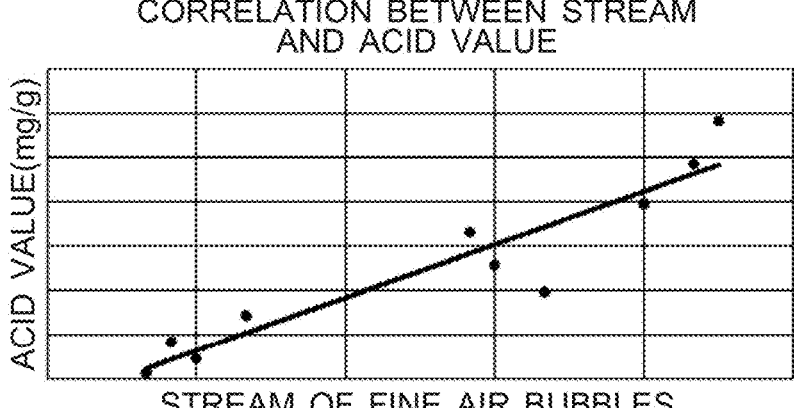
FIG. 13B is a graph illustrating a correlation between the stream of fine air bubbles and the acid value of frying oil.
Figure 13C:
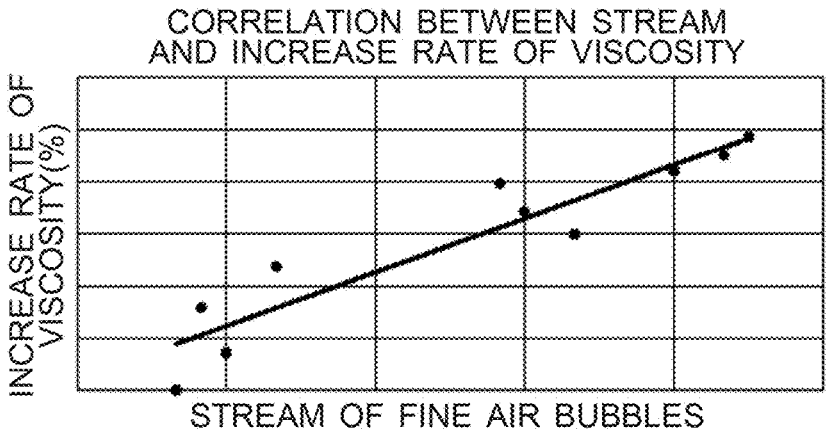
FIG. 13C is a graph illustrating a correlation between the stream of fine air bubbles and the increase rate of viscosity of frying oil.

FIG. 13A illustrates a correlation between the stream of the fine air bubbles β and the color of the frying oil Y, FIG. 13B illustrates a correlation between the stream of the fine air bubbles β and the acid value of the frying oil Y, and FIG. 13C illustrates a correlation between the stream of the fine air bubbles N and the increase rate of viscosity of the frying oil Y. Positive correlations are observed between the stream of the fine air bubbles s and the color of the frying oil Y, the acid value of the frying oil Y, and the increase rate of viscosity of the frying oil Y, respectively.

Figure 14A:
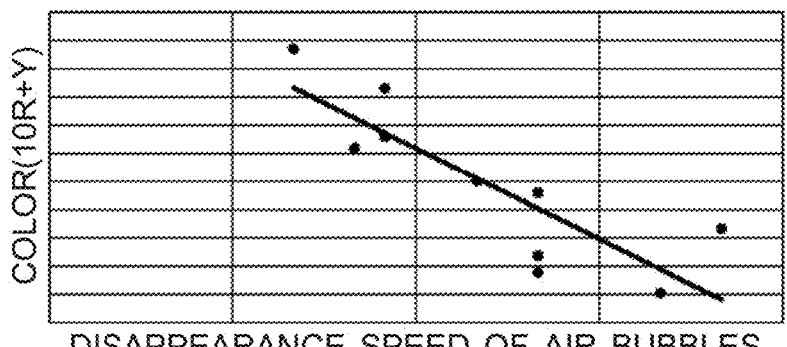
FIG. 14A is a graph illustrating a correlation between the disappearance speed of air bubbles and the color of frying oil.
Figure 14B:
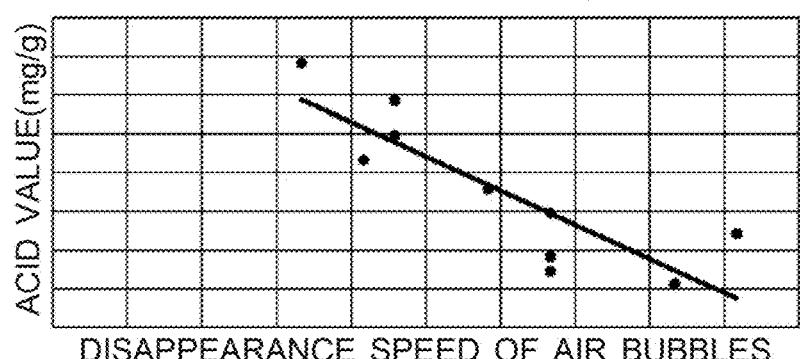
FIG. 14B is a graph illustrating a correlation between the disappearance speed of air bubbles and the acid value of frying oil.
Figure 14C:
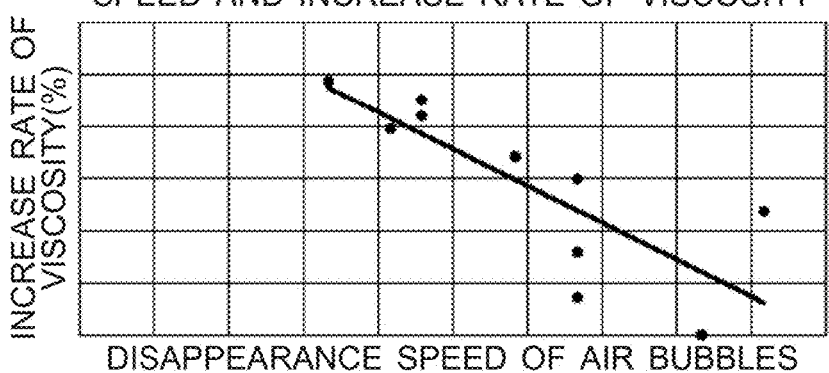
FIG. 14C is a graph illustrating a correlation between the disappearance speed of air bubbles and the increase rate of viscosity of frying oil.

FIG. 14A illustrates a correlation between the disappearance speed of the air bubbles and the color of the frying oil Y, FIG. 14B illustrates a correlation between the disappearance speed of the air bubbles and the acid value of the frying oil Y, and FIG. 14C illustrates a correlation between the disappearance speed of the air bubbles and the increase rate of viscosity of the frying oil Y. Negative correlations are observed between the disappearance speed of the air bubbles and the color of the frying oil Y, the acid value of the frying oil Y, and the increase rate of viscosity of the frying oil Y, respectively. This is because, as the frying oil Y deteriorates, the viscosity of the frying oil Y increases, which makes the air bubbles less likely to disappear.

Figure 15A:
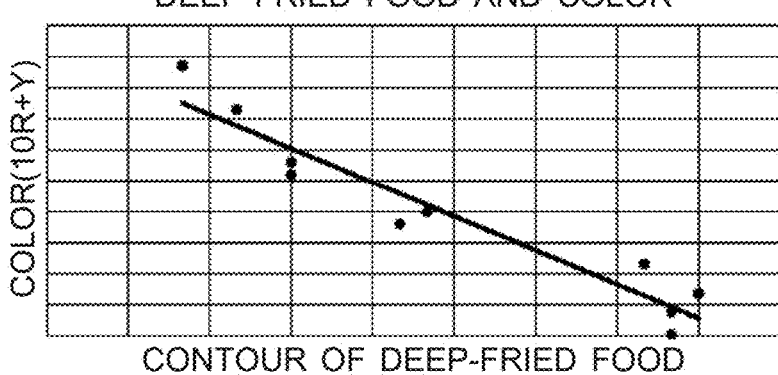
FIG. 15A is a graph illustrating a correlation between the visibility level of the contour of a deep-fried food and the color of frying oil.
Figure 15B:
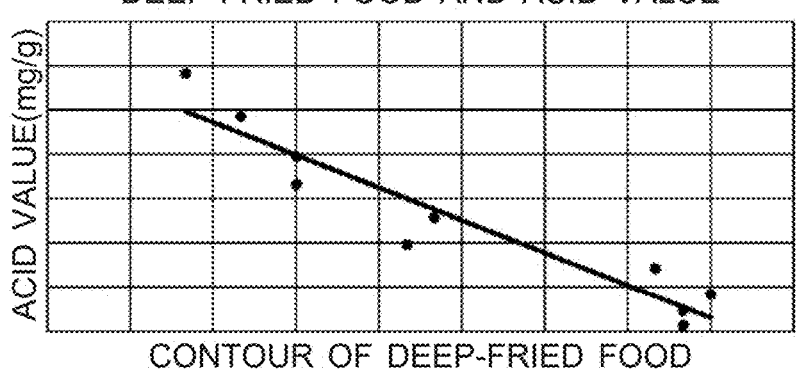
FIG. 15B is a graph illustrating a correlation between the visibility level of the contour of a deep-fried food and the acid value of frying oil.
Figure 15C:
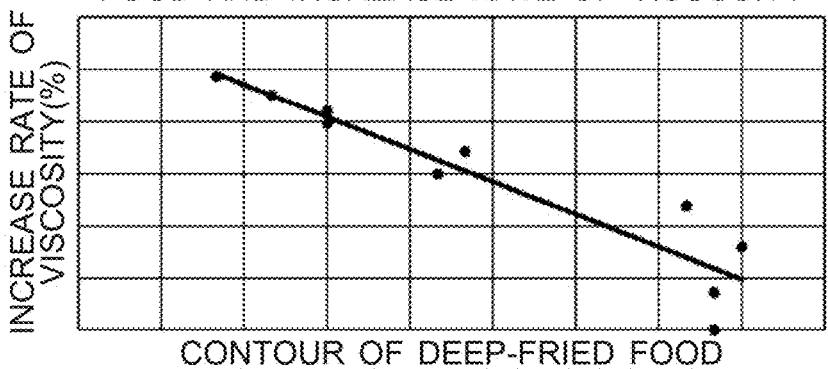
FIG. 15C is a graph illustrating a correlation between the visibility level of the contour of a deep-fried food and the increase rate of viscosity of frying oil.

FIG. 15A illustrates a correlation between the visibility level of the contour of the deep-fried food X and the color of the frying oil Y, FIG. 15B illustrates a correlation between the visibility level of the contour of the deep-fried food X and the acid value of the frying oil Y, and FIG. 15C illustrates a correlation between the visibility level of the contour of the deep-fried food X and the increase rate of viscosity of the frying oil Y. Negative correlations are observed between the visibility level of the contour of the deep-fried food X and the color of the frying oil Y, the acid value of the frying oil Y, and the increase rate of viscosity of the frying oil Y, respectively.

Figure 16A:
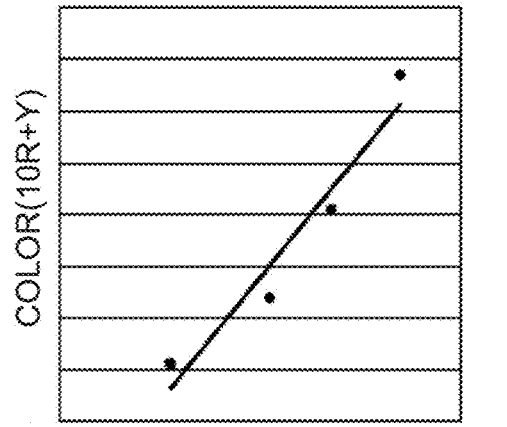
FIG. 16A is a graph illustrating a correlation between the cumulative value of the area of air bubbles and the color of frying oil.
Figure 16B:
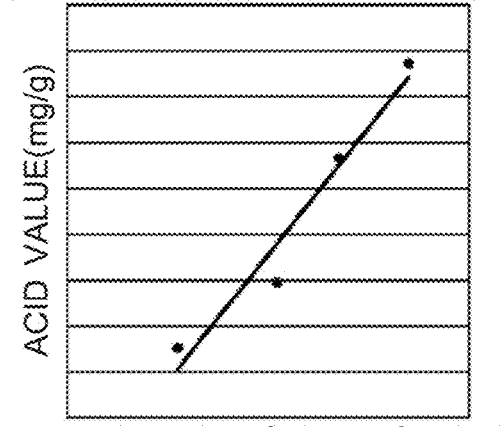
FIG. 16B is a graph illustrating a correlation between the cumulative value of the area of air bubbles and the acid value of frying oil.
Figure 16C:
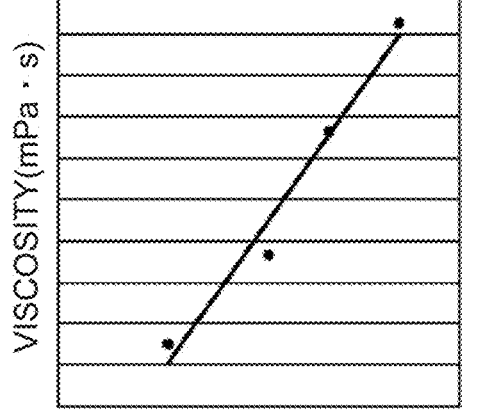
FIG. 16C is a graph illustrating a correlation between the cumulative value of the area of air bubbles and the viscosity of frying oil.

FIG. 16A illustrates a correlation between the cumulative value of the area of air bubbles and the color of the frying oil Y, FIG. 16B illustrates a correlation between the cumulative value of the area of air bubbles and the acid value of the frying oil Y, and FIG. 16C illustrates a correlation between the cumulative value of the area of air bubbles and the viscosity of the frying oil Y. Positive correlations are observed between the cumulative value of the area of air bubbles and the color of the frying oil Y, the acid value of the frying oil Y, and the viscosity of the frying oil Y, respectively.

Note that it is preferable to use a combination of the feature parameters F such as the area ratio of the fine air bubbles β, the number of fine air bubbles β, the disappearance speed of air bubbles, the stream of the fine air bubbles β, the visibility level of the contour of the deep-fried food X, and the cumulative value of the area of the air bubbles. Combining the feature parameters F can improve the precision of estimation of the deterioration indicator DI.

Figure 17:
FIG. 17 is a graph illustrating a correlation between a predicted value and measured value of the acid value.
Figure 17:
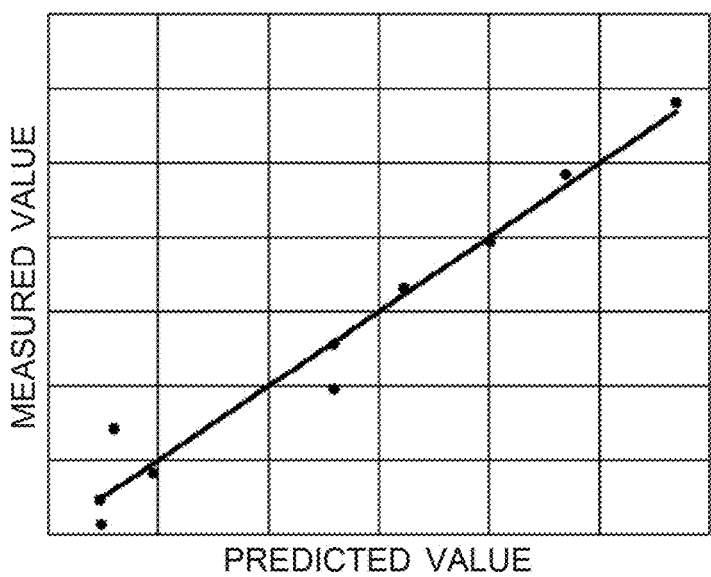

For example, when OPLS analysis (orthogonal projection partial least squares regression) for predicting the acid value of the frying oil Y is performed using a combination of the five feature parameters F, which are the area ratio of the fine air bubbles β, the number of fine air bubbles β, the disappearance speed of air bubbles, the stream of the fine air bubbles β, and the visibility level of the contour of the deep-fried food X, as illustrated in FIG. 17, a positive correlation is found between a predicted value and a measured value. This shows that combining the multiple feature parameters F enables improvement in the precision of prediction of the acid value of the frying oil Y by the indicator relating to the "air bubbles" which can be identified from on the oil surface image when compared to the case of using each of the feature parameters F separately for the prediction.

The deterioration level determination section 56 is configured to determine the deterioration level of the frying oil Y based on the deterioration indicator DI estimated by the deterioration indicator estimation section 55. When the deterioration indicator DI is equal to or more than a deterioration threshold value DIth (DI≥DIth), the deterioration level is 100%, and thus the frying oil Y needs to be changed. When the deterioration indicator DI is less than the deterioration threshold value DIth (DI<DIth), the deterioration level is, for example, 50%, 75%, or the like.

The deterioration threshold value DIth indicating the level of 100% deterioration can be arbitrarily set. For example, it is assumed that a user A sets the acid value 2.5 to the deterioration threshold value DIth (DIth=2.5) and a user B sets the acid value 2.0 to the deterioration threshold value DIth (DIth=2.0). In this case, when both the frying oil Y used for deep-fry cooking performed by the user A and the frying oil Y used for deep-fry cooking performed by the user B have the acid value of 1.0, the deterioration level determination section 56 determines that the deterioration level of the frying oil Y in use by the user A is 40% and the deterioration level of the frying oil Y in use by the user B is 50%.

The change timing decision section 57 is configured to decide whether it is necessary to change the frying oil Y based on the deterioration level determined by the deterioration level determination section 56.

The selection section 58 is configured to select, based on the deterioration level determined by the deterioration level determination section 56, the type of the deep-fried food X which can be deep-fried for the next using the frying oil Y and the number of pieces thereof for each type. Since, depending on the type of the deep-fried food X, the color of the frying oil Y may darken more and/or the viscosity and acid value thereof may increase more, and vice versa, the amount of variation of each of the deterioration indicators differs depending on the type of the deep-fried food X.

Here, the degree of the acid value influenced depending on the deep-fried food X is, for example, "0.01" for fried chickens, "0.005" for croquettes, and "0.002" for hash browns. Based on the above, the number of fried chickens, croquettes, and hash browns which can be deep-fried in the next cooking can be calculated by the following formula (1).

[Formula 1]

$$\Delta AV = 0.01 \times \alpha + 0.005 \times \beta + 0.002 \times \gamma \qquad (1)$$

In Formula (1), ΔAV is a difference (AV1−AV2) between an acid value AV1 serving as a reference when the frying oil Y is to be disposed as waste oil and an acid value AV2 corresponding to the deterioration level of the frying oil Y determined by the deterioration level determination section 56. Furthermore, α is the number of fried chickens, β is the number of croquettes, and γ is the number of hash browns.

For example, where AV1 is "2.5" and AV2 is "1.5", ΔAV is "1.0" (ΔAV=AV1−AV2=2.5−1.5=1.0).

In the case of deep-frying only fried chickens using the frying oil Y, in Formula (1), "1.0" is substituted in ΔAV and "0" is substituted in β and γ, respectively. As a result, α is calculated as "100". This reveals that 100 pieces of fried chickens can be deep-fried using the frying oil Y in the next cooking.

In the case of deep-frying only croquettes using the frying oil Y, in Formula (1), "1.0" is substituted in ΔAV and "0" is substituted in α and γ, respectively. As a result, β is calculated as "200". This reveals that 200 pieces of croquettes can be deep-fried using the frying oil Y in the next cooking.

In the case of deep-frying only hash browns using the frying oil Y, in Formula (1), "1.0" is substituted in ΔAV and "0" is substituted in α and β, respectively. As a result, γ is calculated as "500". This reveals that 500 pieces of hash browns can be deep-fried using the frying oil Y in the next cooking.

In the case of deep-frying each of fried chickens, croquettes, and hash browns on average using the frying oil Y, in Formula (1), "1.0" is substituted in ΔAV and it is set as α=β=γ. As a result, α, β, and γ are all calculated as "58". It reveals that 58 pieces of each of fried chickens, croquettes, and hash browns can be deep-fried using the frying oil Y in the next cooking.

In the case of specifying that 50 pieces of fried chickens are to be deep-fried and only croquettes are to be deep-fried for the other using the frying oil Y, in Formula (1), "1.0" is substituted in ΔAV, "50" is substituted in α, and "0" is substituted in γ, respectively. As a result, β is calculated as "100". This reveals that, in addition to 50 pieces of fried chickens as specified, 100 pieces of croquettes can be deep-fried using the frying oil Y.

In the case of specifying that 50 pieces of fried chickens are to be deep-fried and only hash browns are to be deep-fried for the other using the frying oil Y, in Formula (1), "1.0" is substituted in ΔAV, "50" is substituted in a, and "0" is substituted in β, respectively. As a result, γ is calculated as "250". This reveals that, in addition to 50 pieces of fried chickens as specified, 250 pieces of hash browns can be deep-fried using the frying oil Y.

In the case of specifying that 50 pieces of fried chickens are to be deep-fried and croquettes and hash browns are to be deep-fried for the other pieces on average using the frying oil Y, in Formula (1), "1.0" is substituted in DAV, "50" is substituted in a, respectively, and it is set that β=γ. As a result, both β and γ are calculated as "71". This reveals that, in addition to 50 pieces of fried chickens as specified, 71 pieces of each of the croquettes and hash browns can be deep-fried using the frying oil Y.

The selection section 58 can select the type and number of deep-fried foods X that can be deep-fried using the frying oil Y in the next cooking, using the formula based on the deterioration level (for example, acid value) determined by the deterioration level determination section 56.

As described above, depending on the deterioration level of the frying oil Y, selecting the frying food X suitable for the next deep-fry cooking based on the variation amount of the deterioration indicator DI enables all the deterioration indicators DI to reach the deterioration thresholds DIth at the same time. Furthermore, for example, when the selection section 58 selects the deep-fried food X of the type which absorbs a relatively large amount of oil, adding (mixing) fresh oil by the amount of oil which reduces due to the deep-frying of the deep-fried food X as selected from a predetermined amount can extend the time to dispose the frying oil Y. This can realize the assistance for efficient use of the frying oil Y. Still further, based on the information about the deep-fried food X selected by the selection section 58, the reduced number of deep-fried foods X in the inventory of the store can be managed for the next order of the deep-fried food X.

The notification section 59 is configured to output a display signal (notification signal) related to the deterioration level determined by the deterioration level determination section 56 to the monitor 41. The monitor 41 displays, for example, "present deterioration level of frying oil Y is ○○%".

Furthermore, when the change timing decision section 57 decides that it is time for changing the frying oil Y, the notification section 59 outputs, to the monitor 41, a display signal (notification signal) for displaying the determination result on the monitor 41. The monitor 41 displays, for example, "please change frying oil".

Still further, when the selection section 58 selects the type of the deep-fried food X which can be deep-fried for the next using the frying oil Y and the number of pieces thereof for each type, the notification section 59 outputs, to the monitor 41, a display signal (notification signal) for displaying the selection result and items relating to the selection result on the monitor 41. The monitor 41 displays, for example, "the remaining number of pieces that can be deep-fried is Δ", "Δ pieces of ○○ or Δ pieces of ●● can be deep-fried in the next cooking", "add fresh oil now, and you can use this oil for ○ days later", and the like.

The storage 500 stores the first threshold value range ThR1 and the second threshold value range ThR2, the correlations between the feature parameters F illustrated in FIG. 11 to FIG. 16 and the deterioration indicators DI, the deterioration thresholds DIth, and the correlations between the deterioration level, the type of fried food X, and the number of pieces for each type thereof (for example, Formula (1) described above) and the like, respectively.

(Processing in Deterioration Level Determination Device 5)

Next, a flow of the specific processing executed in the deterioration level determination device 5 will be described with reference to FIG. 18 and FIG. 19.

Figure 18:
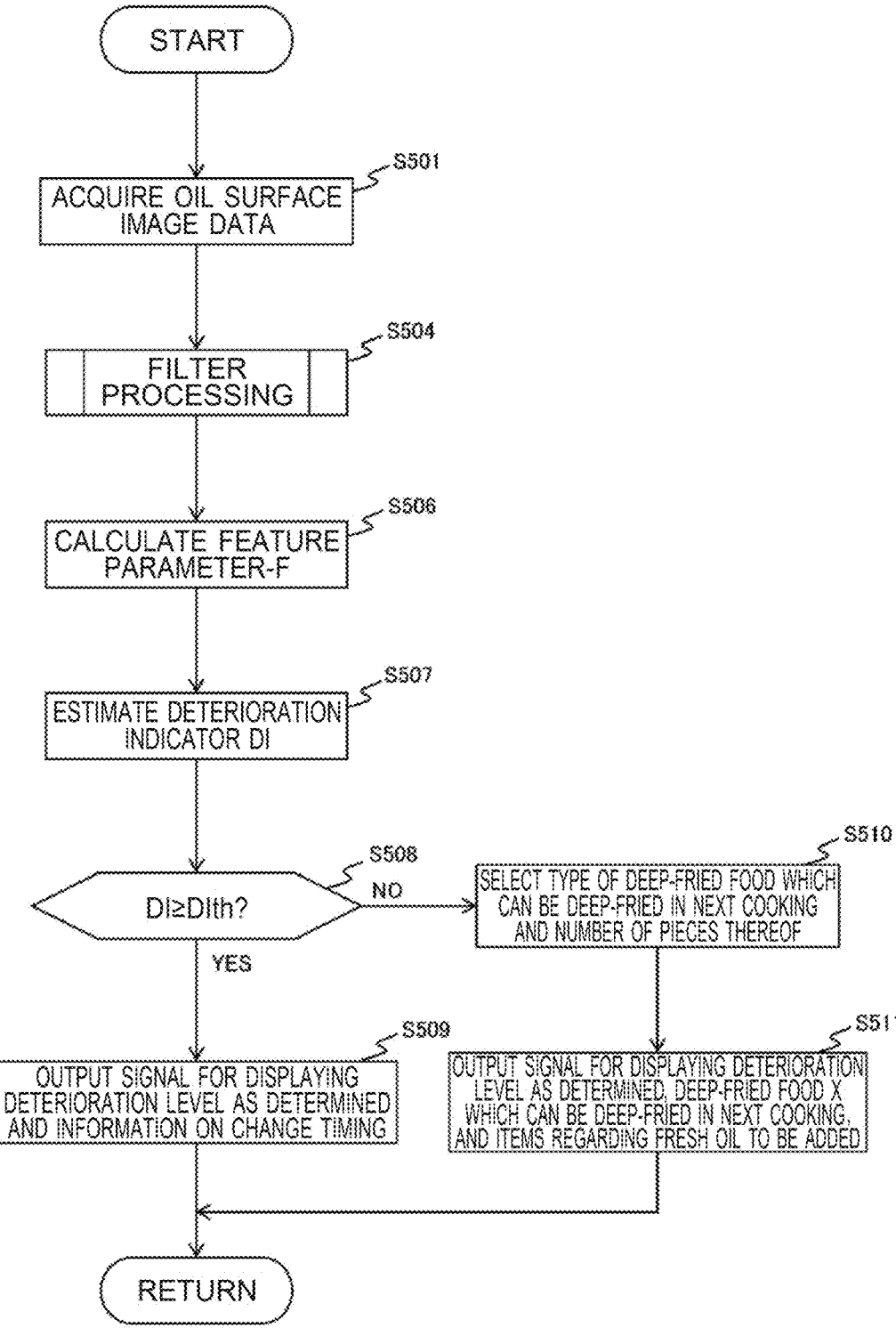
FIG. 18 is a flowchart illustrating a flow of the whole of the processing executed by a deterioration level determination device according to the first embodiment.

FIG. 18 is a flowchart illustrating a flow of the whole of the processing executed by the deterioration level determination device 5 according to the first embodiment. FIG. 19 is a flowchart illustrating a flow of the filter processing.

As illustrated in FIG. 18, firstly, the oil surface image acquisition section 50 acquires the oil surface image data output from the video camera 42 (step S501).

Next, the filter processing section 53 carries out the filter processing on the oil surface image acquired in step S501 to identify the feature area (step S504).

Next, the feature parameter calculation section 54 calculates the feature parameter F in the feature area identified in step S504 (step S506). Note that one or more feature areas may be identified in S504. In the case where a plurality of feature areas is identified, the processing of step S506 is carried out for each of the feature areas as identified. Accordingly, the feature parameters F in the case where a plurality of feature areas is identified may be calculated for each element corresponding to each feature area ("area ratio of fine air bubbles β", "number of fine air bubbles β", and "disappearance speed of fine air bubbles β", etc., as described above). In this case, an average value of each element may be used for the processing described later.

Then, the deterioration indicator estimation section 55 estimates the deterioration indicator DI based on the feature parameter F calculated in step S506 (step S507). The deterioration indicator estimated in step S507 is calculated, as an estimated value, for each element of the feature parameter F based on the correlation data which have been described above.

Subsequently, the deterioration level determination section 56 compares the deterioration indicator DI estimated in step S507 with the deterioration threshold DIth (step S508).

In step S508, if it is determined that the deterioration indicator DI is equal to or more than the deterioration threshold value DIth (DI≥DIth) (step S508/YES), the change timing decision section 57 decides that it is time for changing the frying oil Y, and the notification section 59 outputs, to the monitor 41, a display signal related to the deterioration level (%) determined in step S508 and a display signal informing that it is time for changing the frying oil Y (step S509). Then, the processing in the deterioration level determination device 5 is ended.

In step S508, if it is determined that the deterioration indicator DI is less than the deterioration threshold value DIth (DI<DIth) (step S508/NO), the selection section 58 selects the type and number of pieces of the deep-fried food X which can be deep-fried in the next cooking (step S510). Then, the notification section 59 outputs, to the monitor 41, a display signal related to the deterioration level (%) determined in step S508 and a display signal related to the type of the deep-fried food X selected in step S509 and the number of pieces thereof and the items regarding fresh frying oil to be added based on the selection result in step S509 (step S511). Upon completing the processing of step S511, the deterioration level determination device 5 returns to step S501 and repeats the processing that has been carried out so far.

Thus, estimating the deterioration indicator DI using the feature parameter F calculated based on air bubbles formed on the surface of the frying oil Y after the deep-fried food X is placed therein enables precise determination of the deterioration level of the frying oil Y without depending on the subjectivity of a person who is in charge of determination.

Furthermore, in the present embodiment, among the plurality of air bubbles formed on the surface of the frying oil Y, the feature parameter F of the fine air bubbles β which are frequently formed due to the deterioration of the frying oil Y is used to estimate the deterioration indicator DI so as to determine the deterioration level of the frying oil Y. As a result, compared to the case of estimating the deterioration indicator DI by using the feature parameter F of all air bubbles, it is possible to improve the precision of determination.

Next, the filter processing carried out in step S504 will be described in detail with reference to FIG. 19.

Figure 19:
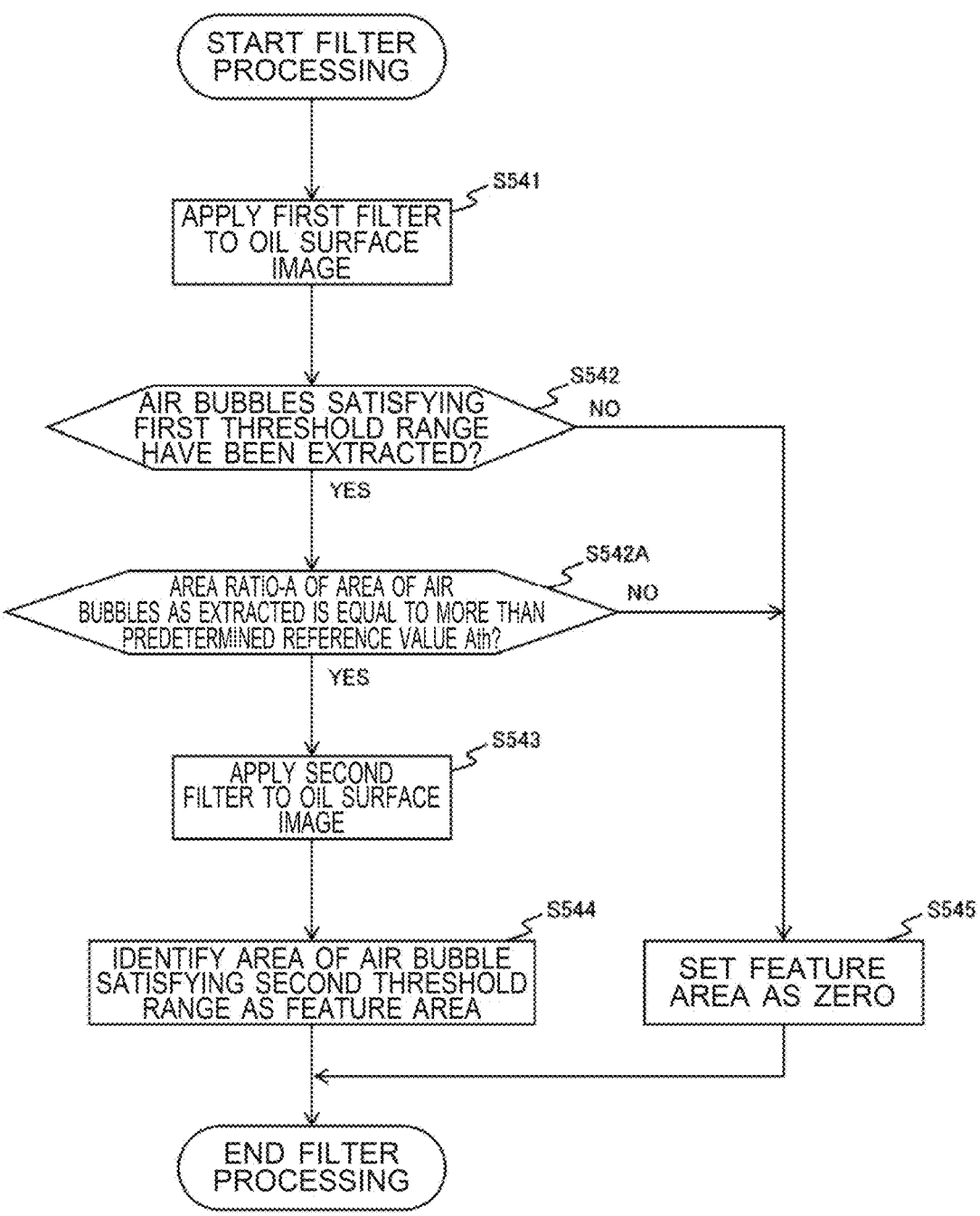
FIG. 19 is a flowchart illustrating a flow of the filter processing.

As illustrated in FIG. 19, in the filter processing, the filter processing section 53 applies a first filter to the oil surface image acquired in step S501 illustrated in FIG. 18 (step S541).

Subsequently, the filter processing section 53 determines whether, within the image area corresponding to the fine air bubbles β, an image area corresponding to the first threshold range ThR1 is extracted from the oil surface image to which the first filter has been applied in step S541 (step S542).

Upon determining in step S542 that the image area corresponding to the first threshold range ThR1 (air bubbles satisfying the first threshold range ThR1) has been extracted (step S542/YES), the filter processing section 53 determines whether the area ratio A of the image area corresponding to the first threshold range ThR1 relative to the whole area of the oil surface image is equal to or more than a predetermined reference value Ath (step S542A). The predetermined reference Ath is stored in the storage 500 (see FIG. 9), and is set to, for example, 0.37%. Note that the predetermined reference value Ath is the value that can be appropriately changed depending on the conditions of image-capturing of the oil surface image and the conditions of deep-frying of the frying food X using the frying oil Y, and is not limited to the value of 0.37%.

Upon determining in step S542A that the area ratio A of the image area corresponding to the first threshold range ThR1 relative to the whole area of the oil surface image is equal to or more than the predetermined reference value Ath (A≥Ath) (step S542A/YES), the filter processing section 53 applies the second filter to the oil surface image acquired in step S501 illustrated in FIG. 18 (step S543).

Next, the filter processing section 53 identifies, within the image area corresponding to the fine air bubbles β extracted from the oil surface image to which the second filter has been applied in step S543, an image area corresponding to the second threshold range ThR2 (area of air bubbles satisfying the second threshold range ThR2) as a feature area (step S544), and ends the filter processing.

On the other hand, upon determining in step S542 that the air bubbles satisfying the first threshold range ThR1 have not been extracted (step S542/NO) and upon determining in step S542A that the area ratio A of the image area corresponding to the first threshold range ThR1 relative to the whole area of the oil surface image is less than the predetermined reference value Ath (A<Ath) (step S542A/NO), the filter processing section 53 sets the feature area to zero (step S545) and ends the filter processing.

As described above, the deterioration level determination device 5 carries out the characteristic filter processing on the oil surface image, thereby identifying a specific area which is the area of the fine air bubbles β which characterize the deterioration of the frying oil Y with high accuracy. In other words, carrying out the filter processing enables the large air bubbles α and the fine air bubbles β to be accurately distinguished from each other, and this can improve the accuracy in the determination of the level of determination more than the case where the filter processing is not carried out on the oil surface image.

Figure 20A:
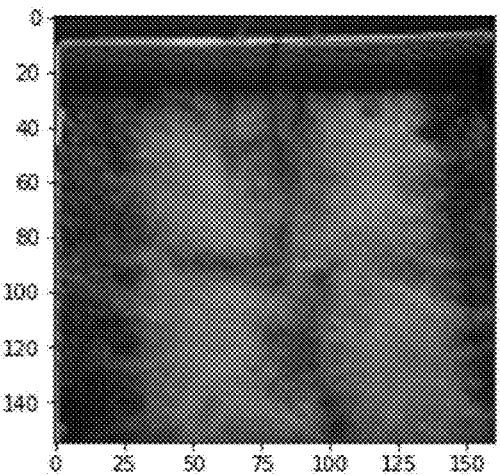
FIG. 20A illustrates an oil surface image during deep-fry cooking of a deep-fried food using fresh frying oil.
Figure 20B:
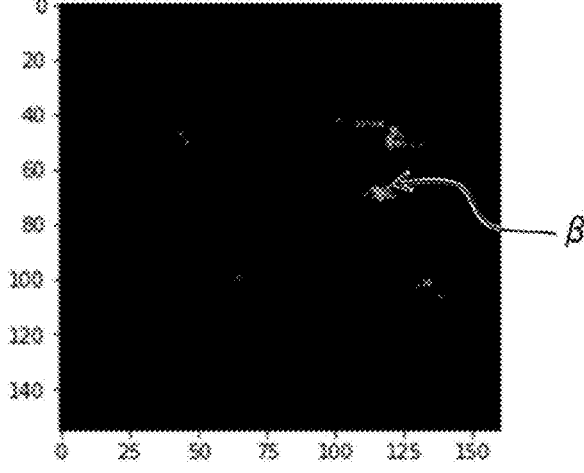
FIG. 20B illustrates the case where the first filter is applied to the oil surface image of FIG. 20A.
Figure 20C:
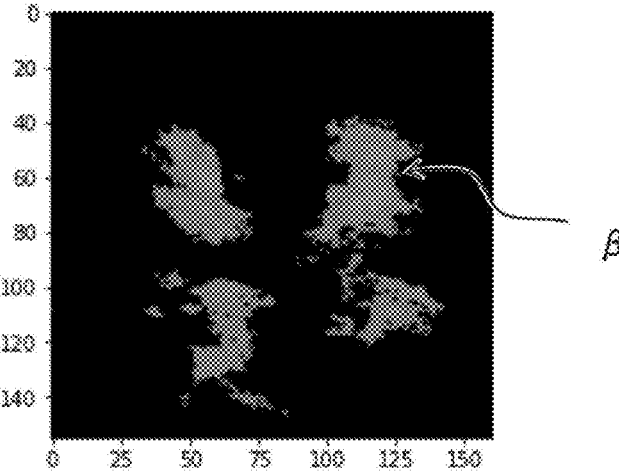
FIG. 20C illustrates the case where the second filter is applied to the oil surface image of FIG. 20A.

FIG. 20A illustrates an oil surface image in which the state of the oil surface during deep-frying of the fried food X using the relatively fresh frying oil Y is captured. FIG. 20B illustrates the case where the first filter is applied to the oil surface image of FIG. 20A. FIG. 20C illustrates the case where the second filter is applied to the oil surface image of FIG. 20A.

As described above, the amount and frequency of formation of the fine air bubbles β are positively correlated with the level of deterioration of the frying oil Y. Typically, the level of deterioration of the frying oil Y progresses in accordance with the increase in the time and number of times the frying oil Y is used. For example, the degree of formation of the fine air bubbles β tends to be low in the case of deep-frying the fried food X using the "relatively fresh frying oil Y" which is almost unused. In this case, regarding the condition of extracting the "fine air bubbles β", the formation of the fine air bubbles β cannot be known with high accuracy by merely carrying out the single filter processing. As in the filter processing described in the present embodiment, as a result of carrying out the first filter processing on the oil surface image of FIG. 20A, almost no air bubble has been extracted that satisfies the first threshold range ThR1, as illustrated in FIG. 20B.

In this case, when the second filter processing is applied to the oil surface image of FIG. 20A, as illustrated in FIG. 20C, the air bubbles satisfying the second threshold range ThR2 are extracted over a certain area. In other words, in the second threshold range ThR2 of which the numerical value range is broader than that of the first threshold range ThR1, there is a possibility that some of the large air bubbles α are extracted together with all the fine air bubbles β included in the oil surface image.

Figure 21A:
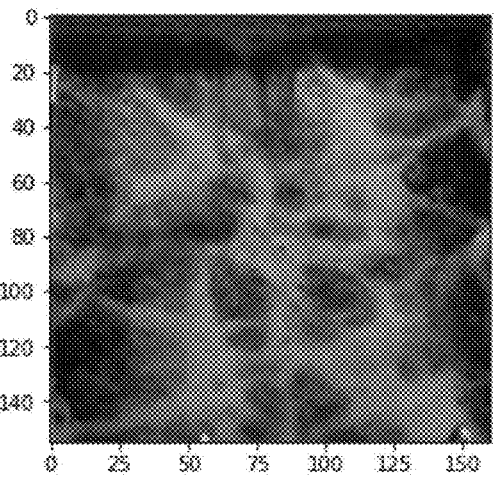
FIG. 21A illustrates an oil surface image during deep-fry cooking of a deep-fried food using deteriorated frying oil.
Figure 21B:
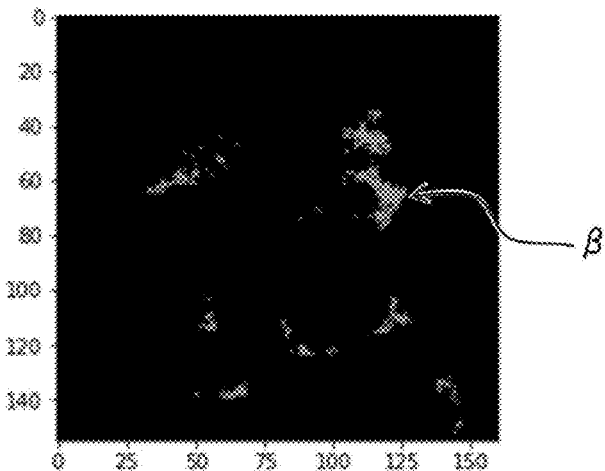
FIG. 21B illustrates the case where the first filter is applied to the oil surface image of FIG. 21A.
Figure 21C:
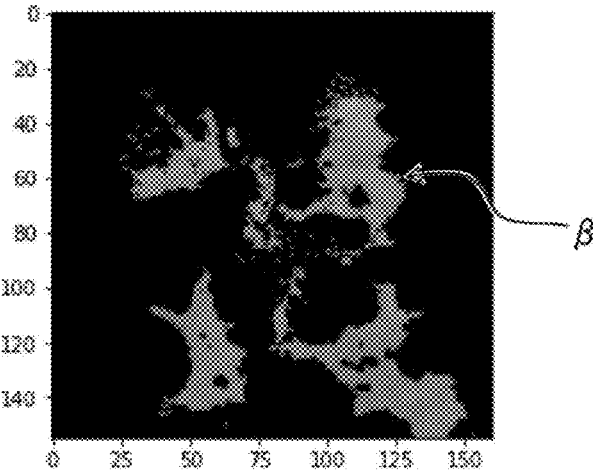
FIG. 21C illustrates the case where the second filter is applied to the oil surface image of FIG. 21A.

On the other hand, FIG. 21A illustrates an oil surface image during deep-frying of the fried food X using the frying oil Y of which the deterioration has progressed to some extent, FIG. 21B illustrates the case where the first filter is applied to the oil surface image of FIG. 21A, and FIG. 21C illustrates the case where the second filter is applied to the oil surface image of FIG. 21A.

The fine air bubbles β are likely to be formed in the case of deep-frying the fried food X using the frying oil Y of which the deterioration has progressed. Accordingly, when the first filter is applied to the oil surface image of FIG. 21A, as illustrated in FIG. 21B, air bubbles satisfying the first threshold range ThR1 are extracted more than the case of FIG. 20B.

In this case, when the second filter processing is applied to the oil surface image in FIG. 21A, as illustrated in FIG. 21C, the air bubbles (fine air bubbles β) satisfying the second threshold range ThR2 are extracted over almost the same area as illustrated in FIG. 20C. However, in the area of the air bubbles satisfying the second threshold range ThR2 illustrated in FIG. 21C, it is found that the number of the large air bubbles α to be extracted is less than that in the area of the air bubbles satisfying the second threshold range ThR2 illustrated in FIG. 20C.

Figure 22A:
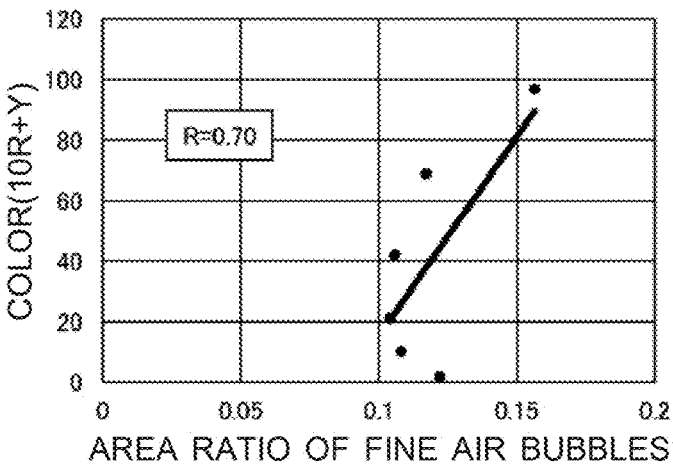
FIG. 22A is a graph illustrating a correlation between the area ratio of fine air bubbles and the color of frying oil in the case of having not applied the filter processing to an oil surface image.
Figure 22B:
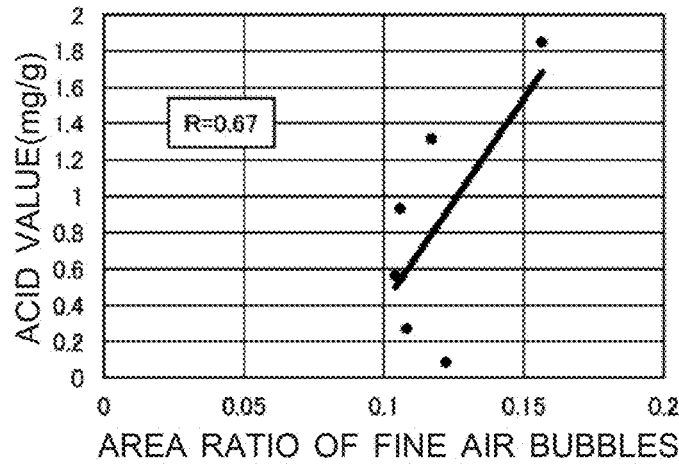
FIG. 22B is a graph illustrating a correlation between the area ratio of fine air bubbles and the acid value of frying oil in the case of having not applied the filter processing to an oil surface image.
Figure 22C:
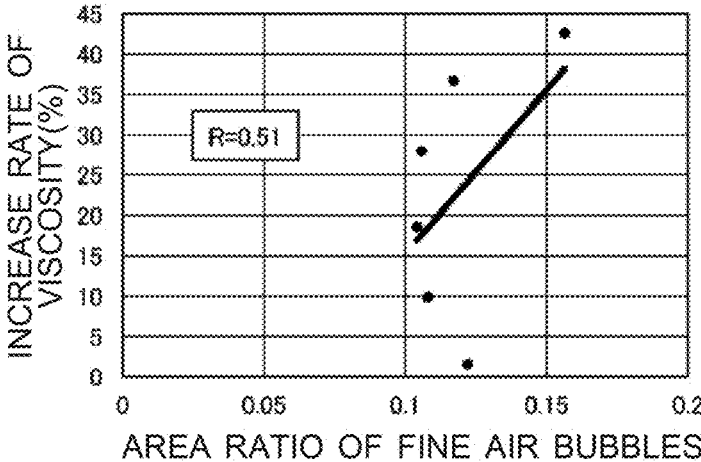
FIG. 22C is a graph illustrating a correlation between the area ratio of fine air bubbles and the increase rate of viscosity of frying oil in the case of having not applied the filter processing to an oil surface image.

FIG. 22A is a graph illustrating a correlation between the area ratio of the fine air bubbles β and the color of the frying oil Y in the case of having not applied the filter processing to the oil surface image, FIG. 22B is a graph illustrating a correlation between the area ratio of the fine air bubbles β and the acid value of the frying oil Y in the case of having not applied the filter processing to the oil surface image, and FIG. 22C is a graph illustrating a correlation between the area ratio of the fine air bubbles β and the increase rate of viscosity of the frying oil Y in the case of having not applied the filter processing to the oil surface image.

In the case where the deterioration level determination device 5 does not carry out the filter processing on the oil surface image, even if the oil surface image does not include the fine air bubbles β, in other words, even in the state in which the oil surface image includes only the large air bubbles α, among the large air bubbles α, the ones having the size close to that of the fine air bubbles β are erroneously extracted as the fine air bubbles β and a specific area is identified. This leads to, as illustrated in FIG. 22A to FIG. 22C, the area ratio of the fine air bubbles β which is 0.1 (10%) or more although the color, acid value, and increase rate of viscosity of the frying oil Y are low, respectively, in other words, although the deterioration has not progressed.

Figure 23A:
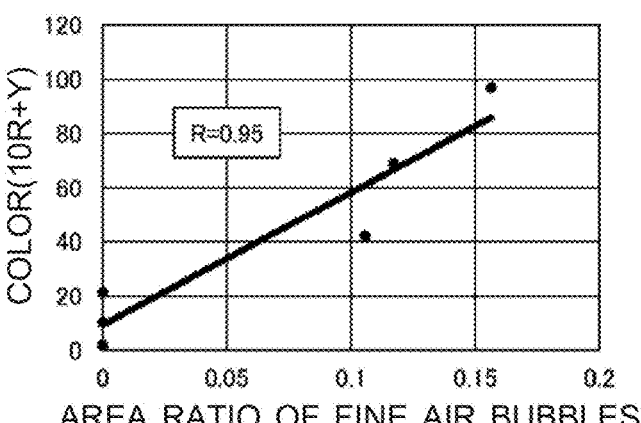
FIG. 23A is a graph illustrating a correlation between the area ratio of fine air bubbles and the color of frying oil in the case of having applied the filter processing to an oil surface image.
Figure 23B:
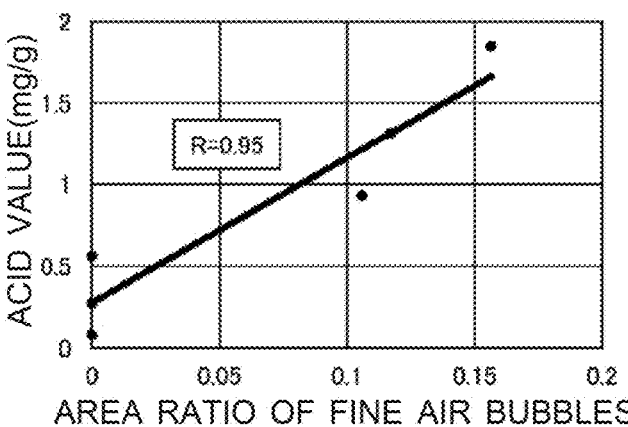
FIG. 23B is a graph illustrating a correlation between the area ratio of fine air bubbles and the acid value of frying oil in the case of having applied the filter processing to an oil surface image.
Figure 23C:
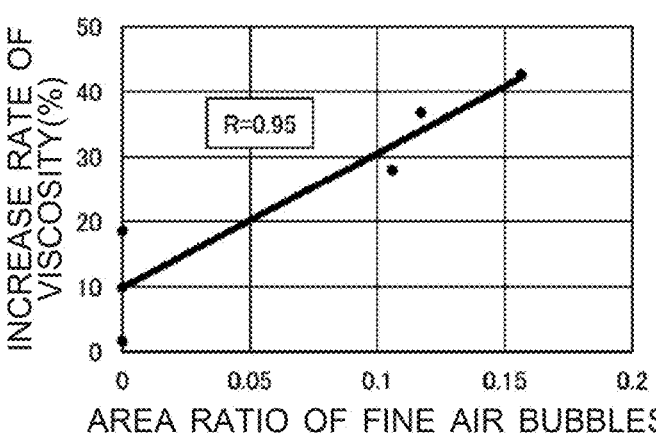
FIG. 23C is a graph illustrating a correlation between the area ratio of fine air bubbles and the increase rate of viscosity of frying oil in the case of having applied the filter processing to an oil surface image.

On the other hand, FIG. 23A is a graph illustrating a correlation between the area ratio of the fine air bubbles β and the color of the frying oil Y in the case of having applied the filter processing to an oil surface image, FIG. 23B is a graph illustrating a correlation between the area ratio of the fine air bubbles β and the acid value of the frying oil Y in the case of having applied the filter processing to an oil surface image, and FIG. 23C is a graph illustrating a correlation between the area ratio of the fine air bubbles β and the increase rate of viscosity of the frying oil Y in the case of having applied the filter processing to an oil surface image.

In the case where the deterioration level determination device 5 carries out the filter processing on the oil surface image, if the oil surface image does not include the fine air bubbles β, in other words, in the state in which the oil surface image includes only the large air bubbles α, the filter processing section 53 sets the feature area to 0. This results in, as illustrated in FIG. 23A to FIG. 23C, the area ratio of the fine air bubbles β which is 0% in the case of the color, acid value, and increase rate of viscosity of the frying oil Y are low, that is, in the state where the deterioration has not progressed.

Figures 24A, 24B:
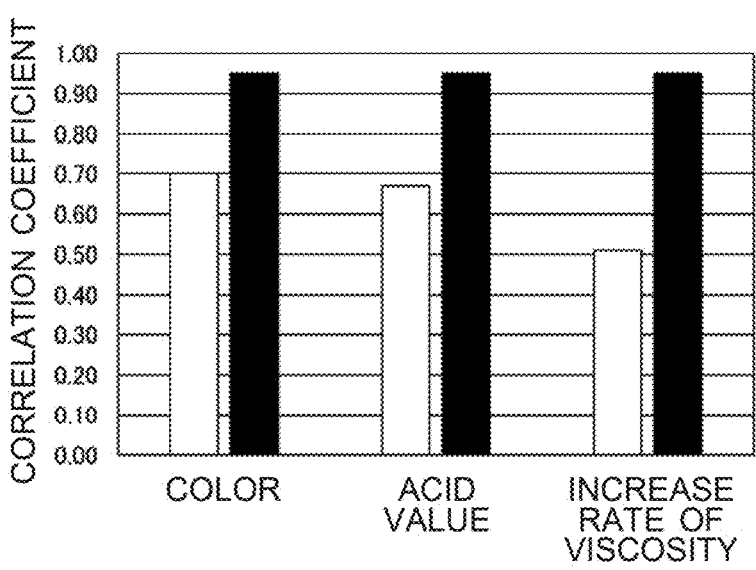
FIG. 24A is a diagram of bar graphs for fried chickens, each illustrating a relation between a deterioration indicator and a correlation coefficient.
FIG. 24B is a diagram of bar graphs for hash browns, each illustrating a relation between a deterioration indicator and a correlation coefficient.

FIG. 24A is a diagram of bar graphs for fried chickens, each illustrating a relation between a deterioration indicator and a correlation coefficient. FIG. 24B is a diagram of bar graphs for hash browns, each illustrating a relation between a deterioration indicator and a correlation coefficient. Here, the "correlation coefficient" depicted in FIG. 24A and FIG. 24B is the coefficient expressing the degree of correlation between the area ratio of the fine air bubbles β and each deterioration indicator DI (color, acid value, and increase rate of viscosity). Furthermore, FIG. 24A expresses the graphs of FIG. 22A to FIG. 22C and FIG. 23A to FIG. 23C as the relations between each deterioration indicator DI and the correlation coefficients.

In FIG. 24A and FIG. 24B, the white-outlined bar graphs represent the case where the deterioration level determination device 5 does not carry out the filter processing on the oil surface image while the black bar graphs represent the case where the deterioration level determination device 5 carries out the filter processing on the oil surface image.

In FIG. 24A, the correlation coefficient is between 0.5 and 0.7 in the case where the deterioration level determination device 5 does not carry out the filter processing on the oil surface image, whereas the correlation coefficient exceeds 0.9 in any deterioration indicator DI in the case where the deterioration level determination device 5 carries out the filter processing on the oil surface image. In FIG. 24B, the correlation coefficient is between 0.7 and 0.8 in the case where the deterioration level determination device 5 does not carry out the filter processing on the oil surface image, whereas the correlation coefficient exceeds 0.9 in any deterioration indicator DI in the case where the deterioration level determination device 5 carries out the filter processing on the oil surface image.

As described above, in the case where the deterioration level determination device 5 carries out the filter processing on the oil surface image, the correlation coefficient is higher than that in the case where the deterioration level determination device 5 does not carry out the filter processing on the oil surface image. That is, the deterioration level determination device 5 carries out the filter processing on the oil surface image, whereby the large air bubbles α and the fine air bubbles β can be definitely distinguished from each other. This allows the fine air bubbles β characterizing the deterioration of the frying oil Y to be extracted from the oil surface image with high accuracy, which can improve the accuracy in the determination of the deterioration level of the frying oil Y.

Furthermore, in the present embodiment, in step S542A illustrated in FIG. 19, only when the area ratio A of the image area corresponding to the first threshold range ThR1 extracted by applying the first filter is equal to or more than the predetermined reference value Ath (A≥Ath) (step S542A/YES), the second filter is applied to the oil surface image in step S543. This enables the noise (false positive fine air bubbles β) to be removed and realizes further enhancement of the accuracy in the determination of the deterioration level of the frying oil Y.

In other words, in step S542A illustrated in FIG. 19, when the area ratio A of the image area corresponding to the first threshold range ThR1 extracted by applying the first filter is less than the predetermined reference value Ath (A<Ath), the image area as extracted is highly likely to be the noise, and thus the processing needs to proceed to step S545 to set the feature area to zero.

Note that the deterioration level determination device 5 does not necessarily have to carry out the processing of step 542A (determination as to whether the area ratio A of the image area corresponding to the first threshold range ThR1 extracted by applying the first filter is equal to or more than the predetermined reference value Ath). In this case, the processing may proceed to step S543 if the image area corresponding to the first threshold range ThR1 is extracted in step S542 (step S542/YES).

For carrying out the filter processing by the filter processing section 53A, it is preferable to distinguish the large air bubbles α and the fine air bubbles β to some extent in advance. Specifically, the large air bubbles α and the fine air bubbles β are distinguished from each other focusing on the nature of the fine air bubbles β.

The fine air bubbles β tend to crowd and gather easily more than the large air bubbles α. Using this nature, for example, when the number of pixels adjacent to the color (whitish color) of the fine air bubbles β exceeds a predetermined reference value (for example, the area ratio of 2.5%), the area is extracted as the area of the fine air bubbles β. This prevents extraction of a whitish area, if detected, as the fine air bubbles β if the number of adjacent pixels does not exceed a predetermined reference value.

Furthermore, the fine air bubbles β are less likely to disappear than the large air bubbles α. Using this nature, the fine air bubbles β can be extracted based on the length of time during which the air bubbles remain in the image captured by the video camera 42.

Still further, air bubbles are layers of air, the temperature thereof is lower than that of the frying oil Y, and the fine air bubbles β have the tendency to gather, and thus it can be considered that the temperature of the fine air bubbles β is lower than that of the large air bubbles α. Using this nature, for example, the temperature of the surface of the frying oil Y is measured, and a predetermined area having the temperature lower than the temperature of the frying oil Y can be extracted as the area of the fine air bubbles β. For example, thermography can be used to capture the difference in temperature.

Still further, using the nature that the fine air bubbles β are formed with the progress of deterioration of the frying oil Y, the fine air bubbles β are extracted more accurately by considering how long the frying oil Y has been used. How long the frying oil Y has been used is the indicator corresponding to the cumulative use time of the frying oil Y. For example, in the case where the video camera 42 continues to capture an oil image at a frequency of one image per five seconds, the fine air bubbles β are extracted in consideration of the cumulative time in which "the number of captured images×5 seconds".

Second Embodiment

Next, a deterioration level determination device 5A according to the second embodiment of the present invention will be described with reference to FIG. 25 and FIG. 26.

Figure 25:
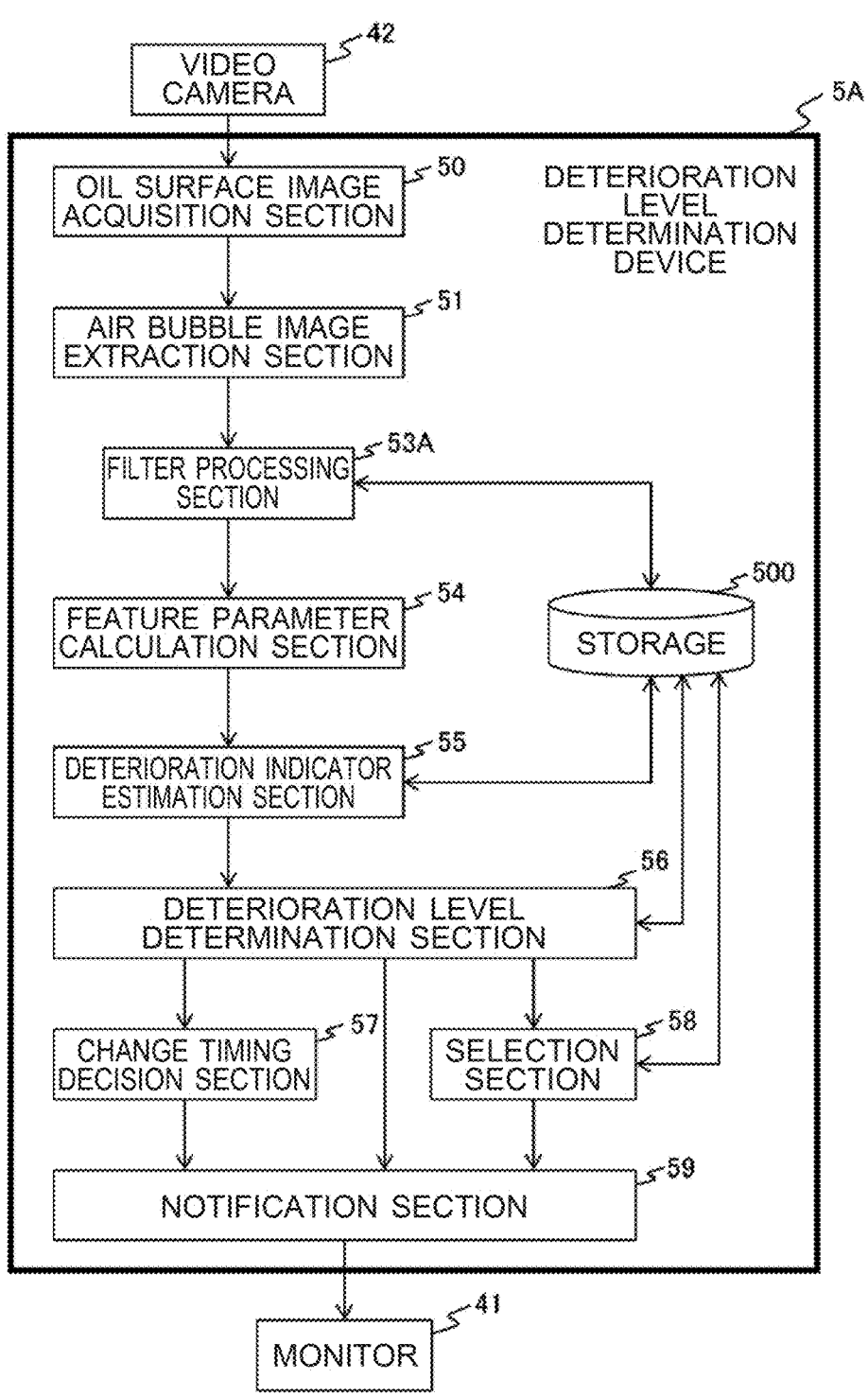
FIG. 25 is a functional block diagram illustrating functions of a deterioration level determination device according to the second embodiment.

FIG. 25 is a functional block diagram illustrating the functions of the deterioration level determination device 5A according to the second embodiment. FIG. 26 is a flowchart illustrating a flow of the whole processing executed by the deterioration level determination device 5A according to the second embodiment.

Figure 26:
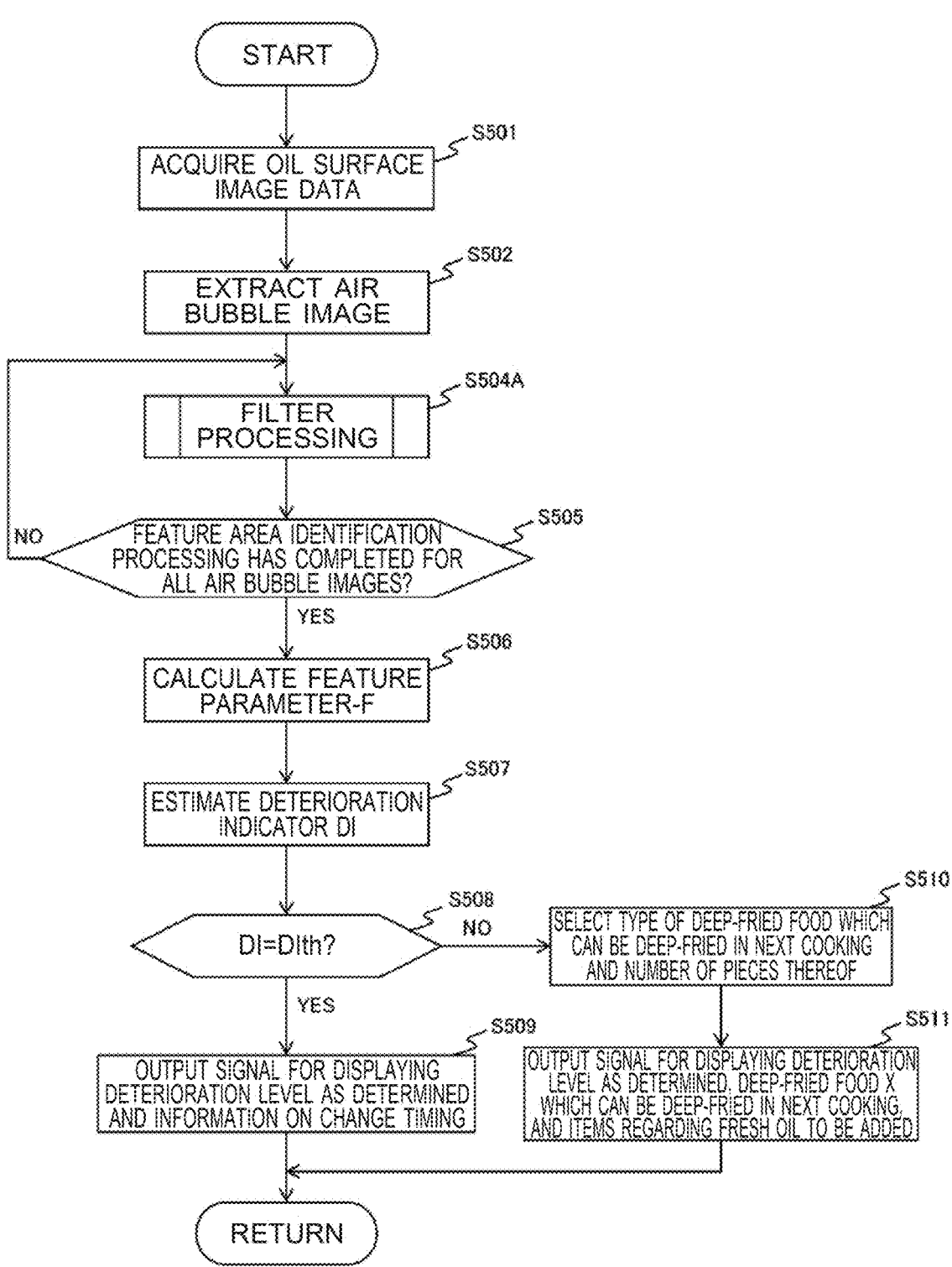
FIG. 26 is a flowchart illustrating a flow of the whole of the processing executed by a deterioration level determination device according to the second embodiment.

In FIG. 25 and FIG. 26, the components common to those described for the deterioration level determination device 5 according to the first embodiment are provided with the same reference signs, and explanation thereof is omitted. The same applies to the third to fifth embodiments.

As illustrated in FIG. 25, the deterioration level determination device 5A according to the present embodiment includes an air bubble image extraction section 51 in addition to the nine function sections (oil surface image acquisition section 50, filter processing section 53A, feature parameter calculation section 54, deterioration indicator estimation section 55, deterioration level determination section 56, change timing decision section 57, selection section 58, notification section 59, and storage 500) included in the deterioration level determining device 5 according to the first embodiment.

The air bubble image extraction section 51 is configured to extract, as an "air bubble image", a portion (area) corresponding to the air bubbles formed due to deep-fry cooking from the oil surface image acquired by the oil surface image acquisition section 50. For example, the air bubble image extraction section 51 executes the contour extraction image processing using the filter processing on the oil surface image. In the contour extraction image processing, an image of the area including a portion that matches the feature of an air bubble (for example, approximates a circular shape) from a portion forming the contour (portion indicating a certain enclosed area) included in the oil surface image is extracted as an "air bubble image".

Then, the filter processing section 53A carries out the filter processing on the air bubble image extracted from the oil surface image by the air bubble image extraction section 51. The filter processing section 53 according to the first embodiment carries out the filter processing directly on the oil surface image acquired by the oil surface image acquisition section 50. On the other hand, the filter processing section 53A according to the present embodiment does not carry out the filter processing directly on the oil surface image but on the air bubble image extracted from the oil surface image, which differs from the filter processing section 53 according to the first embodiment.

As illustrated in FIG. 26, in the deterioration level determination device 5A, when the oil surface image acquisition section 50 acquires the oil surface image data (step S501), then, the air bubble image extraction section 51 extracts the air bubble image from the oil surface image data as acquired (step S502).

Next, the filter processing section 53A carries out the filter processing on the air bubble image extracted in step S502 to identify a specific area from the air bubble image (step S504A). The target of the filter processing executed in step S504A is not the oil surface image but the air bubble image while the content of the processing is the same as that of the filter processing in the first embodiment. In step S504A, all the areas in the air bubble image which have been identified as the air bubbles are the targets of the processing.

Next, the filter processing section 53A determines whether the filter processing of step S504A has been completed for all the air bubble images extracted in step S502 (step S505).

If it is determined in step S505 that the filter processing has not completed for all the air bubble images (step S505/NO), the processing returns to step S504A. On the other hand, if it is determined in step S505 that the filter processing has been completed for all the air bubble images (step S505/YES), the processing proceeds to step S506 and thereafter.

Third Embodiment

Next, a deterioration level determination system 100a according to the third embodiment of the present invention will be described with reference to FIG. 27 and FIG. 28.

Figure 27:
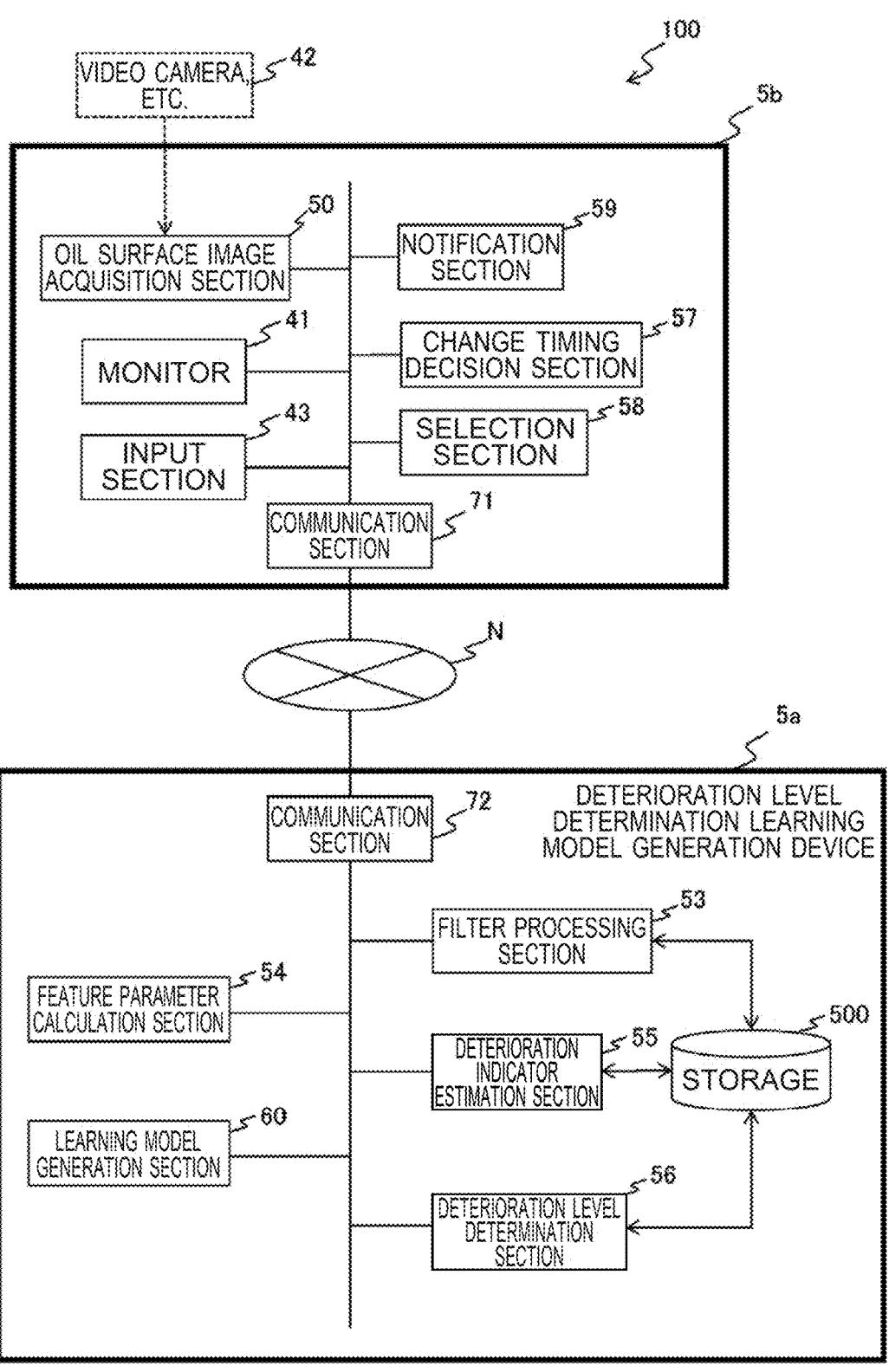
FIG. 27 is a functional block diagram illustrating functions of a deterioration level determination device according to the third embodiment.
Figure 28:
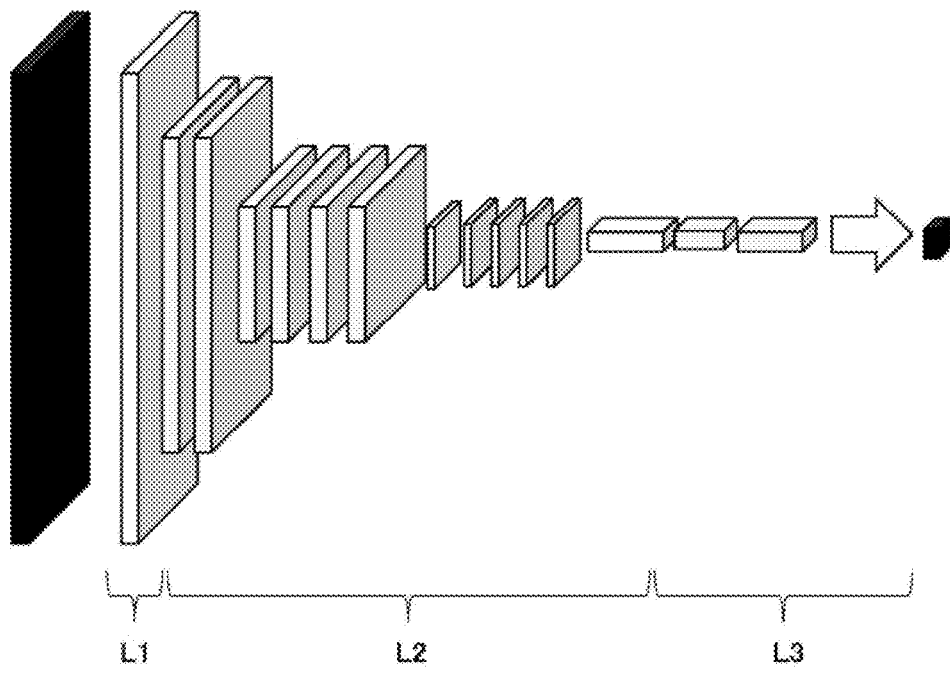
FIG. 28 illustrates an example of a network structure.

FIG. 27 is a functional block diagram illustrating the functions of the deterioration level determination system 100a according to the third embodiment. FIG. 28 illustrates an example of a network structure.

The deterioration level determination system 100a according to the present embodiment includes a deterioration level determination learning model generation device 5a. The deterioration level determination learning model generation device 5a is configured to generate a learning model for determining the deterioration level of frying oil by using data including a plurality of data sets in which oil surface images of the fry basket 3 captured at arbitrary times (timings) while the user is performing deep-fry cooking are associated with various indicators related to determination of the deterioration level of the frying oil in the fry basket 3 at that time.

The deterioration level determination learning model generation device 5a and a terminal device 5b connected thereto by communication via a communication network N provide input interfaces of the oil surface image related to the frying oil, respectively.

Here, various indicators related to the determination of the level of deterioration include the ones listed for the first embodiment, which are information obtained by measurement by the image processing on an oil surface image, such as "the area ratio of a feature area relative to the whole area of an oil surface image", "a cumulative value of the area ratio of a feature area relative to the whole area of an oil surface image", "the number of the fine air bubbles β included in a feature area", "the disappearance speed of the fine air bubbles β included in a feature area (time from formation of the fine air bubbles β to disappearance thereof)", "the presence or absence of a stream of the fine air bubbles β included in a feature area", and "the difference between the color of the frying oil Y and the color of the area of the deep-fried food X (visibility level of the contour of the deep-fried food X)". Various indicators also include measurement information about the frying oil Y and the deep-fried food X, such as "the viscosity of the frying oil Y", "an increase rate of viscosity of the frying oil Y", "an acid value (AV) of the frying oil Y", "the color of the frying oil Y", and "the quantity of volatile compounds of the deep-fried food X", and information such as the type of the frying oil Y, the type and number of pieces of the fried food X, and the like.

The deterioration level determination system 100a uses a learning model generated based on the data as exemplified above to update the data in the storage 500 provided in the deterioration level determination learning model generation device 5a that is communicatively connected to the terminal device 5b used by a user via the communication network N, thereby improving the precision of determination of the deterioration level of the frying oil.

The deterioration level determination learning model generation device 5a may be configured to generate the learning model per user who creates and inputs the data. In this case, when performing the determination of the deterioration level of the frying oil using a learning model, each user uses only the learning model generated based on the data provided by each user themselves. This enables determination of the deterioration specifically to each user's cooking environment (the type of frying oil Y to be used, the type of deep-fried food X).

The deterioration level determination learning model generation device 5a may be configured to generate the learning model without distinguishing units of users who create and input data. In this case, the learning model can be generated using a larger amount of data. When the generated learning model is used, the deterioration level of the frying oil is determined using the characteristics (the type of frying oil Y, the type and number of deep-fried foods X), which are predefined per user unit, and the oil surface image as input data. This enables highly precise deterioration determination using a learning model with a larger amount of machine learning based on the cooking environments of a plurality of users (the type of frying oil Y, the type and number of deep-fried foods X).

The terminal device 5b includes the same configuration as that of the deterioration level determination device 5 according to the first embodiment, that is, the oil surface image acquisition section 50, the change timing decision section 57, the selection section 58, and the notification section 59, and further includes a communication section 71. Furthermore, the terminal device 5b includes a monitor 41 for displaying a result of determination and an input unit 43 for inputting data. The input unit 43 includes an input device for inputting text information and numerical information by user's operation, such as a mouse and a keyboard, and a data reading device for reading a group of data stored in a storage medium.

Similarly, the deterioration level determination learning model generation device 5a, which is one of the aspects of a machine learning device, includes the same configuration as that of the deterioration level determination device 5 according to the first embodiment, that is, the filter processing section 53, the feature parameter calculation section 54, the deterioration indicator estimation section 55, the deterioration level determination section 56, and the storage 500, and further includes a communication section 72 and a learning model generation section 60.

The filter processing section 53 identifies, as the feature area, the area of a portion allowing the state of the fine air bubbles β which changes as the progress of the deep-fry cooking using the frying oil Y to be acquired. The communication section 71 and the communication section 72 provide the functions including interfaces for information communication with each other via the communication network N, respectively.

Furthermore, each of the oil surface image acquisition section 50, the filter processing section 53, the feature parameter calculation section 54, the deterioration indicator estimation section 55, the deterioration level determination section 56, the change timing decision section 57, the selection section 58, the notification section 59, and the storage 500, which has the same configuration as the corresponding one of the deterioration level determination device 5 according to the first embodiment, provides the same function.

These functions are implemented by remotely installed hardware resources, and connecting them in a communicative manner enables implementation of the same functions and processing flows as those of the deterioration level determination device 5 according to the first embodiment.

Based on the feature parameter F calculated by the learning model generation section 60 and the feature parameter calculation section 54, so-called machine learning is executed, and using indicator data (explanatory variables) stored in advance in the storage section 500, for example, a calibration line (model equation) is generated by, for example, linear regression, support vector machine (SVM), bugging, boosting, AdaBoost, decision tree, random forest, logistic regression, neural network, deep learning, in deep learning, especially a convolution neural network (CNN) and recurrent neural network (RNN), long short-term memory (LSTM), or the like.

As the type of linear regression (analysis), for example, single regression, multiple regression, partial least-squares (PLS) regression, and orthogonal projection partial least squares (OPLS: orthogonal partial least squares) regression have been known. At least one of these types can be selected and used.

Single regression is an approach for predicting one objective variable by one explanatory variable while multiple regression is an approach for predicting one objective variable by a plurality of explanatory variables. The (orthogonal projection) partial least squares regression is an approach for extracting principal components corresponding to small features (obtained by principal component analysis with explanatory variables only) so that the covariance between the principal components and the objective variable is maximized. The (orthogonal projection) partial least squares regression is a suitable approach when the number of explanatory variables is greater than the number of samples and the correlation among explanatory variables is strong.

By applying the calibration curve obtained by the machine learning in the learning model generation section 60 to the oil surface image acquired through the oil surface image acquisition section 50, it is possible to estimate the deterioration level of the frying oil Y and thus provide the estimation result.

AI according to the learned model of the present embodiment has a network structure including an input layer L1, an intermediate layer L2, an output layer L3. Specifically, it is the one including a Convolution Neural Network (CNN) or the like as illustrated in FIG. 28.

The input layer L1 is a layer for inputting an image, to which oil surface image data that is data of an image of the frying oil Y in oil vat 21 (see FIG. 1) and cooking data that indicates the content of the current deep-fry cooking are input, respectively. An image relating to customer data may also be input to the input layer L1, in addition to the oil surface image data and cooking data to be input as the oil image data.

The intermediate layer L2 is a layer for processing such as convolution, pooling, normalization, or a combination thereof with respect to the image input in the input layer L1.

The output layer L3 is a layer for outputting a result obtained by the processing by the intermediate layer L2. For example, the output layer L3 is configured with a fully-connected layer or the like.

Convolution is the process for generating a feature map, based on, for example, a filter, a mask, a kernel (hereinafter, simply referred to as "filter"), or the like, by filtering on an image or filtering a feature map generated by a predetermined process on the image.

Specifically, the filter is data used for multiplying a pixel value of an image or feature map by a filter coefficient (may be referred to as "weight" or "parameter"). The filter coefficient is a value defined by learning, setting, or the like. The convolution process is the process of multiplying a pixel value of each pixel forming the image or feature map by a filter coefficient to generate a feature map having a calculation result as its component.

As a result of the convolution process described above, features of the image or those of the feature map can be extracted. The features are, for example, edge components or a result of statistical process of a periphery of a target pixel. Furthermore, as a result of the convolution process, even from an image or feature map in which a subject indicated thereby is vertically shifted, horizontally shifted, obliquely shifted, rotated, or have an attitude of a combination thereof, the similar features can be extracted.

Pooling is the process of extracting features to generate a feature map by performing the process such as calculation of an average, extraction of a minimum value, or extraction of a maximum value on a target area. That is, pooling is max pooling, avg pooling, or the like. Note that convolution and pooling may include preprocessing such as Zero Padding.

By performing the processes described above such as convolution, pooling, or a combination thereof, so-called effects of reduction in data amount, compositionality, translation invariance, or the like can be obtained.

Normalization is the process of, for example, equalizing variances and averages. Note that normalization may be performed locally. Normalization causes the data to have values within a predetermined range. This makes the data to be easily handled in subsequent processing.

Fully connected is the process of dropping data, such as a feature map or other data, into the output. For example, data is output in the binary format, such as "YES" or "NO". In this type of output format, fully-connected is the process of joining the nodes based on the features extracted in the intermediate layer L2 so that either of the two types is the conclusion.

On the other hand, in the case of three or more types of outputs, fully connected is the process of performing a so-called soft max function or the like. As described above, the fully connected process allows classification (including outputs indicating probabilities) to be performed by the maximum likelihood estimation.

Fourth Embodiment

Next, an oil and fat change system 200 according to the fourth embodiment of the present invention will be described with reference to FIG. 29.

Figure 29:
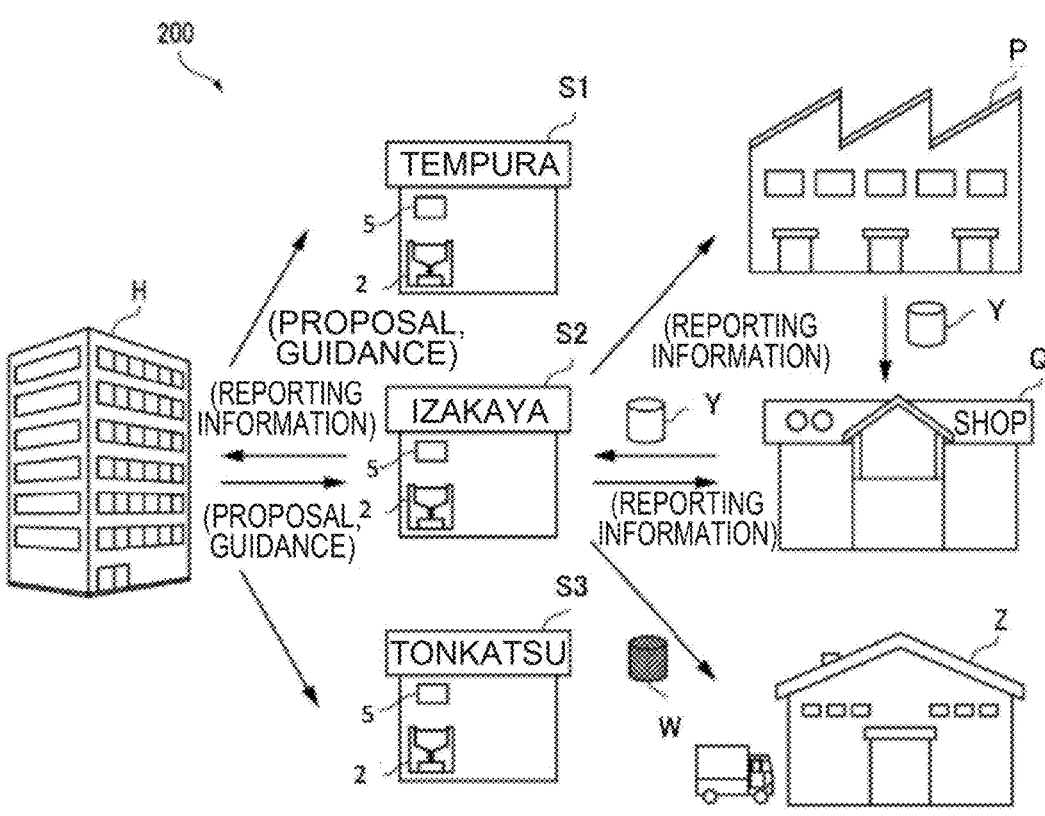
FIG. 29 is a diagram for explaining an oil and fat change system according to the fourth embodiment.

As illustrated in FIG. 29, the oil and fat change system 200 includes shops S1 to S3 each of which is provided with the deterioration level determination device 5 and the fryer 2, a headquarters H for controlling and managing the shops S1 to S3, a manufacturer (oil and fat manufacturer) X of frying oil used in the shops S1 to S3, a seller (wholesaler or store) Q, and a disposal company Z that collects waste oil. Since the oil and fat manufacturer may sell oil directly to customers, the seller Q is a concept including the oil and fat manufacturer.

In the first embodiment, when it is determined that the deterioration level of the frying oil Y exceeds a predetermined threshold value, the notification section 59 of the deterioration level determination device 5 notifies the user of the information by means of the monitor 41 or the like. In the present embodiment, in addition to such notification, the notification section 59 outputs reporting information regarding the deterioration level of the frying oil Y. The reporting information may include the content that the deterioration level of the frying oil Y has exceeded the threshold value, or may be a forecast that the deterioration level is about to exceed the threshold value soon.

As illustrated in FIG. 29, upon receiving the reporting information from the shop S2 (izakaya), the headquarters H analyzes the number of times that the reporting information is received, frequency thereof, and the like. Then, the headquarters H provides suggestions or guidance as to whether the usage the frying oil is appropriate, the frying oil is appropriately changed, the usage is not wasteful, and the like, not only to the shop S2 but also to the shop S1 (tempura restaurant) and the shop S3 (tonkatsu restaurant) as necessary.

The headquarters H is not limited to a position to manage a plurality of shops and stores, but may manage a plurality of factories provided with fryers. The headquarters H may also manage a plurality of fryers 2 provided in a store or a factory.

The manufacturer P of frying oil and the seller Q of frying oil are also notified of this reporting information. Upon receiving the reporting information, the manufacturer P forms a manufacturing plan or a sales plan for frying oil. Furthermore, upon receiving the reporting information, the seller Q orders and purchases the fresh frying oil Y from the manufacturer P. Then, the seller Q distributes the fresh frying oil Y to the shop S2 (also to the shop S1 and the shop S3 if necessary).

Still further, the disposal company Z (may be the manufacturer P) of the frying oil Y is notified of this reporting information. Upon receiving the reporting information, the disposal company Z arranges collection of waste oil W. For example, when receiving the reporting information for a predetermined number of times, the disposal company Z visits the shop S2 to collect the waste oil W from the oil vat 21 of the fryer 2.

Still further, the reporting information may be notified to a cleaning operator (not illustrated). Upon receiving the reporting information, the cleaning operator visits the shop S2 to clean the inside of the oil vat 21 of the fryer 2 and thereabround. Thus, it is possible to quickly perform a series of operations including supply of frying oil to the shops S1 to S3, disposal of waste oil, and cleaning.

Automation of change of the frying oil Y in the shops and stores based on the content of the notification would enable the reduction in the burden on a user (employee in the shops and stores). In this case, output of the reporting information indicating that the deterioration level of the frying oil Y exceeds the threshold value automatically triggers the initiation of change of the frying oil Y.

Fifth Embodiment

Next, a deterioration level determination terminal 9 according to the fifth embodiment of the present invention will be described with reference to FIG. 30A, FIG. 30B, and FIG. 31.

Figure 30A:
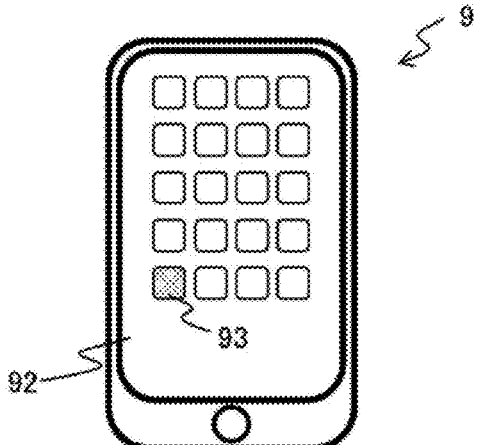
FIG. 30A illustrates an example of a configuration of a deterioration level determination terminal according to the fifth embodiment, which is a front view of the deterioration level determination terminal as viewed from the side of a display.
Figure 30B:
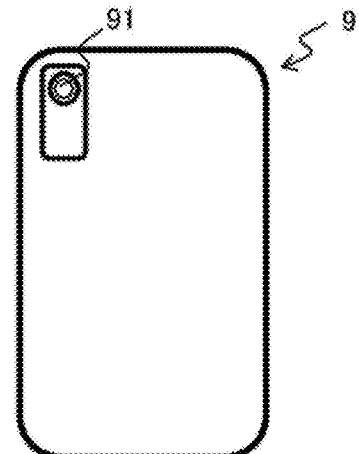
FIG. 30B illustrates an example of a configuration of a deterioration level determination terminal according to the fifth embodiment, which is a rear surface view of the deterioration level determination terminal as viewed from the side of an image capturing section.

FIG. 30A is a front view of the deterioration level determination terminal 9 as viewed from the side of a display 92. FIG. 30B is a rear surface view of the deterioration level determination terminal 9 as viewed from the side of an image capturing unit 91. FIG. 31 is a functional block diagram exemplifying a configuration of a functional module made available upon execution of an application 93 for deterioration level determination by the hardware similar to the information processing device provided in the deterioration level determination terminal 9.

The deterioration level determination terminal 9 according to the present embodiment is the terminal having a communication function in addition to the functions similar to those of the information processing device, which is assumed to be so-called a "smartphone". The deterioration level determination terminal 9 is used by a person who cooks deep-fried foods, and is held so that the surface portion of the frying oil Y is within an angle of view of the deterioration level determination terminal 9 mainly during the deep-fry cooking thereof.

In the other embodiments described above, the video camera 42 (image capturing device), the deterioration level determination device 5, 5A, and the monitor 41 (notification device) are configured as separate hardware. However, the present invention is not limited to the hardware configuration described above in carrying out the "edible oil deterioration determination" characterized in the present invention. For example, as illustrated in FIG. 30A and FIG. 30B, the deterioration level determination terminal 9 (smartphone) on which the image capturing unit 91, the display 92, and the application 93 for determination of deterioration level of the frying oil Y are mounted can be used.

Figure 31:
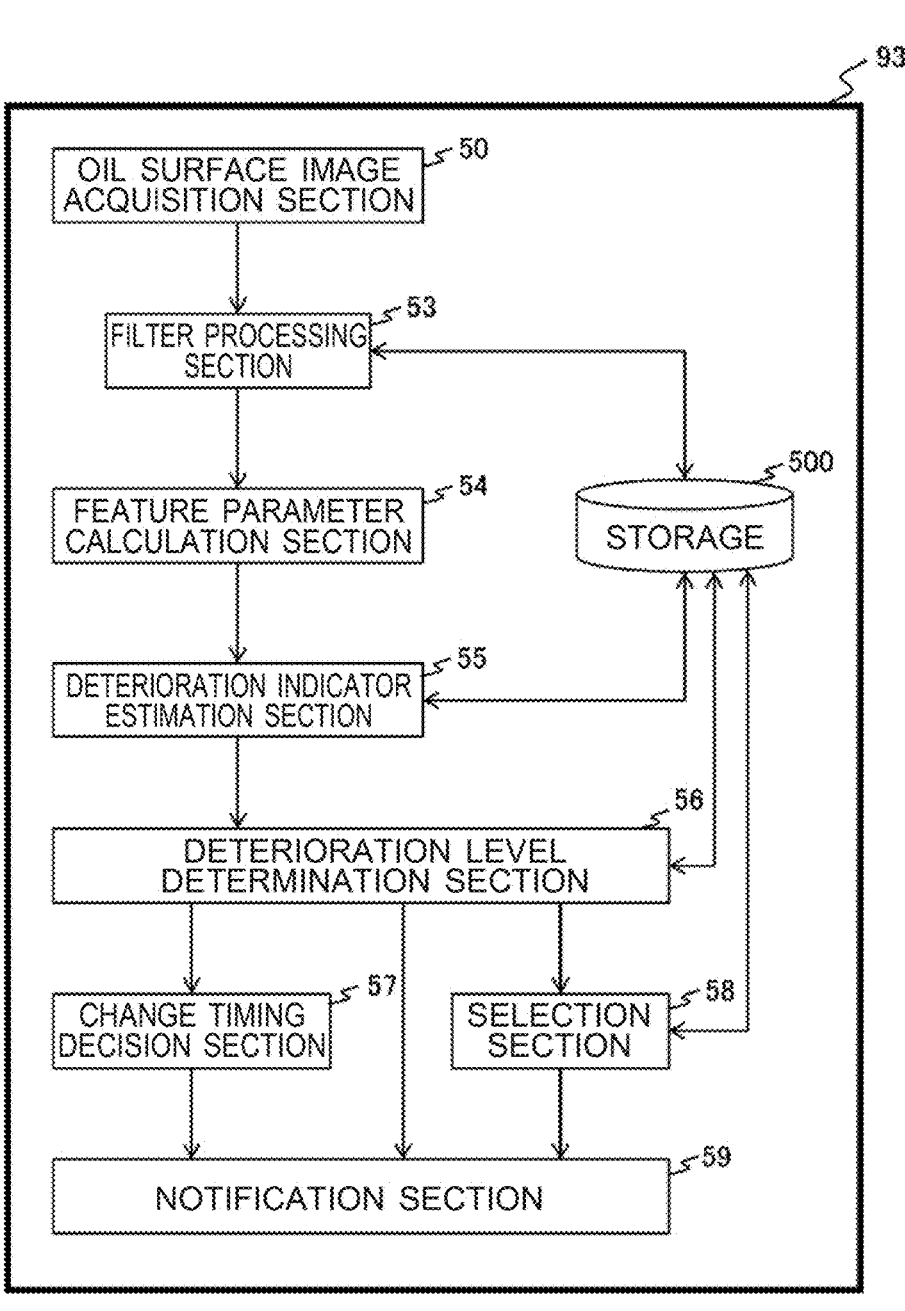
FIG. 31 is a functional block diagram illustrating functions of a deterioration level determination terminal according to the fifth embodiment.

As illustrated in FIG. 31, the deterioration level determination terminal 9 has the same functional blocks as those of the deterioration level determination device 5 (see FIG. 9), and can execute the deterioration level determination processing described above. Thus, the edible oil deterioration level determination method according to the present invention is not limited to a stationary type information processing device, and can be applied to a mobile information processing terminal having a communication function or the like.

In the above, the present invention has been described with reference to each of the embodiments of the present invention. The present invention is not limited to the embodiments described above, and various modifications may be made therein. For example, each of the embodiments is described in detail herein for the purpose of clarity and a concise description, and the present invention is not necessarily limited to those including all the features described above. Furthermore, some of the features according to a predetermined embodiment can be replaced with other features according to the separate embodiments, and other features can be added to the configuration of a predetermined embodiment. Still further, some of the features can include other features of the separate embodiments, be deleted, and/or replaced.

REFERENCE SIGNS LIST

5, 5A: deterioration level determination device
5a: deterioration level determination learning model generation device (machine learning device)
21: oil vat
41: monitor (notification device)
42: video camera (image capturing device)
50: oil surface image acquisition section (oil image acquisition section)
51: air bubble image extraction section
53: filter processing section
54: feature parameter calculation section
55: deterioration indicator estimation section
56: deterioration level determination section
57: change timing decision section
58: selection section
59: notification section
100: deterioration level determination system
L1: input layer
L2: intermediate layer
L3: output layer
Y: frying oil (edible oil)

The invention claimed is:

1. An edible oil deterioration level determination device for determining a deterioration level of an edible oil, comprising:

an oil image acquisition section configured to acquire an oil image that is an image of the edible oil;

a filter processing section configured to apply filter processing to the oil image acquired by the oil image acquisition section, the filter processing being carried out for identifying a feature area that is an area of predetermined air bubbles characterizing deterioration of the edible oil based on a range of a color of air bubbles included in the oil image;

a feature parameter calculation section configured to calculate a feature parameter that is a parameter characterizing the deterioration of the edible oil in the feature area identified by the filter processing section;

a deterioration indicator estimation section configured to estimate a deterioration indicator of the edible oil based on the feature parameter calculated by the feature parameter calculation section; and a deterioration level determination section configured to determine the deterioration level of the edible oil based on the deterioration indicator estimated by the deterioration indicator estimation section.

2. The edible oil deterioration level determination device according to claim 1, wherein the filter processing includes:

first filter processing using a first threshold range set to a specific color range allowing the predetermined air bubbles that are portions of the air bubbles from the oil image; and second filter processing using a second threshold range of which a specific color range is set to be broader than that of the first threshold range, and the filter processing section applies the second filter processing to the oil image based on a result of the first filter processing that has been applied to the oil image.

3. The edible oil deterioration level determination device according to claim 2, wherein the filter processing section applies the second filter processing to the oil image upon determining that the oil image includes the predetermined air bubbles as a result of applying the first filter processing to the oil image.

4. The edible oil deterioration level determination device according to claim 1, further comprising an air bubble image extraction section configured to extract an air bubble image that is an image of a portion corresponding to air bubbles from the oil image acquired by the oil image acquisition section, wherein the filter processing section applies the filter processing to the air bubble image extracted by the air bubble image extraction section.

5. The edible oil deterioration level determination device according to claim 1, wherein the feature parameter includes one or more parameters selected from an area ratio of the feature area relative to a whole area of the oil image, a cumulative value of the area ratio of the feature area relative to the whole area of the oil image, the number of the predetermined air bubbles included in the feature area, disappearance speed of the predetermined air bubbles included in the feature area, and presence or absence of a stream of the predetermined air bubbles included in the feature area.

6. The edible oil deterioration level determination device according to claim 1, wherein the deterioration indicator includes one or more indicators selected from a viscosity of the edible oil, an increase rate of viscosity of the edible oil, an acid value (AV) of the edible oil, a color of the edible oil, an anisidine value of the edible oil, a polar compound value of the edible oil, a carbonyl value of the edible oil, a smoke point of the edible oil, a tocopherol content of the edible oil, an iodine value of the edible oil, a refractive indicator of the edible oil, a quantity of volatile compounds of the edible oil, a composition of volatile compounds of the edible oil, a flavor of the edible oil, a quantity of volatile compounds of a fried food obtained by deep-fry cooking using the frying oil, a composition of volatile compounds of the fried food obtained by deep-fry cooking using the frying oil, and a flavor of the fried food obtained by deep-fry cooking using the frying oil.

7. The edible oil deterioration level determination device according to claim 1, further comprising a notification section configured to output, to a notification device, a notification signal related to the deterioration level of the edible oil determined by the deterioration level determination section.

8. The edible oil deterioration level determination device according to claim 7, further comprising a selection section configured to select a type of a fried food that can be deep-fried using the edible oil and the number for each type thereof based on the deterioration level of the edible oil determined by the deterioration level determination section, wherein the notification section further outputs a notification signal related to a content selected by the selection section to the notification device.

9. The edible oil deterioration level determination device according to claim 7, further comprising a change timing decision section configured to decide whether it is time to change the edible oil based on the deterioration level of the edible oil determined by the deterioration level determination section, wherein when the change timing decision section decides that it is time to change the frying oil, the notification section further outputs a notification signal related to a result of decision that has been made by the change timing decision section.

10. An edible oil deterioration level determination system for determining a deterioration level of an edible oil, comprising:

an image capturing device that is installed above an oil vat in which the edible oil is stored to capture an oil image that is an image of the edible oil; and a deterioration level determination device for determining the deterioration level of the edible oil based on the oil image, the deterioration level determination device being configured to:

acquire the oil image output from the image capturing device;

apply filter processing to the oil image, the filter processing being carried out for identifying a feature area that is an area of predetermined air bubbles characterizing deterioration of the edible oil based on a range of a color of air bubbles included in the oil image;

calculate a feature parameter that is a parameter characterizing the deterioration of the edible oil in the feature area;

estimate a deterioration indicator of the edible oil based on the feature parameter as calculated; and determine the deterioration level of the edible oil based on the deterioration indicator as estimated.

11. An edible oil deterioration level determination method of determining a deterioration level of an edible oil, comprising:

acquiring an oil image that is an image of the edible oil;

applying filter processing to the oil image as acquired, the filter processing being carried out for identifying a feature area that is an area of predetermined air bubbles characterizing deterioration of the edible oil based on a range of a color of air bubbles included in the oil image;

calculating a feature parameter that is a parameter characterizing the deterioration of the edible oil in the feature area;

estimating a deterioration indicator of the edible oil based on the feature parameter as calculated; and determining the deterioration level of the edible oil based on the deterioration indicator as estimated.

* * * * *